US011320396B2

(12) United States Patent
Yan et al.

(10) Patent No.: US 11,320,396 B2
(45) Date of Patent: May 3, 2022

(54) ELECTRONIC DEVICE INCLUDING GAS SENSOR AND METHOD OF OPERATING THE SAME

(71) Applicant: Samsung Electronics Co., Ltd., Suwon-si (KR)

(72) Inventors: Long Yan, Hwaseong-si (KR); Jeong-ho Park, Seoul (KR); Hyun-surk Ryu, Hwaseong-si (KR); Min-chul Lee, Seongnam-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 489 days.

(21) Appl. No.: 16/356,480

(22) Filed: Mar. 18, 2019

(65) Prior Publication Data
US 2020/0096476 A1     Mar. 26, 2020

(30) Foreign Application Priority Data

Sep. 21, 2018  (KR) ........................ 10-2018-0114374

(51) Int. Cl.
*G01N 27/416* (2006.01)
*H03H 9/17* (2006.01)
*H03H 9/10* (2006.01)
*H03H 9/02* (2006.01)

(52) U.S. Cl.
CPC ..... *G01N 27/4162* (2013.01); *H03H 9/02007* (2013.01); *H03H 9/1007* (2013.01); *H03H 9/172* (2013.01)

(58) Field of Classification Search
CPC .......... G01N 27/4162; G01N 33/0009; G01N 29/036; G01N 2291/014; G01N 29/022; G01N 2291/021; G01N 2291/106; H03H 9/02007; H03H 9/1007; H03H 9/172
See application file for complete search history.

(56) References Cited

U.S. PATENT DOCUMENTS

| 5,647,047 A | 7/1997 | Nagasawa |
| 9,217,675 B2 | 12/2015 | Yang et al. |
| 2012/0119791 A1 | 5/2012 | Hsiao |
| 2017/0212100 A1 | 7/2017 | Kwak et al. |
| 2017/0292926 A1 | 10/2017 | Mayer et al. |
| 2017/0318136 A1 | 11/2017 | Han et al. |

FOREIGN PATENT DOCUMENTS

| JP | 2000-162172 A | 6/2000 |
| KR | 10-0299204 | 10/2001 |
| KR | 10-1265788 | 7/2012 |
| KR | 10-1362430 | 2/2014 |

*Primary Examiner* — Xin Y Zhong
(74) *Attorney, Agent, or Firm* — Harness, Dickey & Pierce, P.L.C.

(57) ABSTRACT

An electronic device includes a pop-up device configured to be inserted into a main body of the electronic device in an inserted state, including a gas sensor including a sensor block for sensing a gas, and configured to expose the sensor block to an outer portion of the electronic device in a pop-up state; a power supplier arranged on an outer portion of the pop-up device, configured to supply electric power to the gas sensor; and a connection controller configured to control a connection state of the pop-up device, to block supply of electric power to the gas sensor when the pop-up device is in the inserted state and to supply electric power to the gas sensor when the pop-up device is in the pop-up state, including one or more terminals formed on the pop-up device that move together with the pop-up device when the pop-up device moves.

20 Claims, 14 Drawing Sheets

ELECTRONIC DEVICE INCLUDING GAS SENSOR AND METHOD OF OPERATING THE SAME

CROSS-REFERENCE TO RELATED APPLICATION

This application claims the benefit of Korean Patent Application No. 10-2018-0114374, filed on Sep. 21, 2018, in the Korean Intellectual Property Office, the disclosure of which is incorporated herein in its entirety by reference.

BACKGROUND

Inventive concepts relate to an electronic device, and more particularly, to an electronic device including a gas sensor and a method of operating the electronic device.

A gas sensor that may sense and measure smell, gas, etc. may be applied to various kinds of systems (or devices). Various kinds of gas sensors may be applied to a system, as an example, in a gas sensor using a film bulk acoustic resonator (FBAR), a predetermined material (e.g., polymer, etc.) reacting to a kind of gas that is to be sensed is coated on the FBAR, and a resonant characteristic of the FBAR varies depending on the coated material.

In order for a gas sensor to operate, a sensing material that is sensitive to moisture and gas needs to be exposed to the outside and combined with gas molecules due to its characteristics. Thus, it is difficult to mount a gas sensor in a mobile device, such as a smartphone, for example. Also, in the case of a gas sensor based on FBAR, when an FBAR coated with a sensing layer is exposed to the outside for a long period of time, the gas sensor may be easily contaminated according to an environment in which the gas sensor is used. As a result, the performance of the gas sensor may degrade and a utilization time (or lifespan) of the gas sensor may be reduced. However, it is difficult to replace the gas sensor according to the conventional art. In addition, in a gas sensor based on an FBAR, electric power and a clock signal need to be supplied for performing a gas sensing operation, and a configuration of performing data processing by using sensing information from the gas sensor is needed. However, conventional mobile devices are not equipped with a gas sensor, and the conventional art lacks a mechanism or technique for the management of supply of the electric power and clock to the gas sensor. Thus, there are limitations existing in the conventional art when applying the gas sensor to a system (or device).

SUMMARY

Inventive concepts provide an electronic device including a gas sensor, the electronic device preventing (or reducing) degradation of characteristics such as an accuracy, a sensitivity, etc. of the gas sensor and increasing lifespan of the gas sensor, and a method of operating the electronic device including the gas sensor. To address the aforementioned problems associated with the conventional art, a pop-up device (e.g., in the form of a stylus pen), a part of which may be exposed to the outside (e.g., open air, surrounding atmosphere, external environment) according to a manual manipulation of a user or automated control by the electronic device itself based on certain factors, is included in an electronic device (e.g., a mobile device such as a smartphone), and a gas sensor based on FBAR is mounted in the pop-up device. Accordingly, a portion of the pop-up device protrudes outward from the electronic device, and the gas sensor is exposed to the outside to perform a gas sensing operation. Also, a connecting state between a conductive line for transferring electric power from a power generator and a clock signal from a clock generator in the electronic device, and terminals formed on an outer surface of the pop-up device, for example, is controlled differently according to whether the pop-up device is in an inserted state or in a pop-up state with respect to the electronic device. For example, when the pop-up device is inserted into a main body of the electronic device (inserted state), the connection is disconnected (or disabled) and transfer of the electric power and clock signal to the gas sensor is blocked (or prevented). On the other hand, when part of the pop-up device protrudes from the electronic device such that the gas sensor mounted therein is exposed to the outside (pop-up state), the connection is connected (or enabled) and the electric power and the clock signal are transferred to the gas sensor. As compared to the conventional art, various technological improvements or technical advantages of the electronic device including the pop-up device according to example embodiments of the inventive concepts include, but are not limited to, enabling the gas sensor to be mounted in the electronic device (e.g., by implementing the gas sensor in a stylus pen that is insertable into a mobile device such as a smartphone), preventing (limiting or reducing) contamination and degradation of performance, accuracy, sensitivity, etc. of the gas sensor, enabling an amount of electric power consumed to sense the gas to be reduced, extending the usable lifespan of the gas sensor, and enabling the gas sensor to be replaced easily (e.g., simply by replacing the stylus pen in which the gas sensor is mounted, due to contamination/performance degradation or when reaching the end of its lifespan).

According to some example embodiments of the inventive concepts, there is provided an electronic device including: a pop-up device configured to be inserted into a main body of the electronic device in an inserted state of the pop-up device and including a gas sensor including a sensor block for sensing a gas, the pop-up device being configured to expose the sensor block to an outer portion of the electronic device in a pop-up state of the pop-up device in which at least a part of the pop-up device protrudes outward from the electronic device; a power supplier arranged on an outer portion of the pop-up device, the power supplier being configured to supply electric power to the gas sensor; and a connection controller configured to control a connection state of the connection controller, so as to block supply of the electric power to the gas sensor when the pop-up device is in the inserted state, and to supply the electric power to the gas sensor when the pop-up device is in the pop-up state, wherein the connection controller includes one or more terminals formed on the pop-up device, and the one or more terminals move together with the pop-up device when the pop-up device moves.

According to some example embodiments of the inventive concepts, there is provided an electronic device including: a pop-up device configured to be inserted into a main body of the electronic device in an inserted state of the pop-up device and including a gas sensor for sensing a gas, the pop-up device being configured to expose the gas sensor at least partially to an outer portion of the electronic device in a pop-up state of the pop-up device in which at least a part of the pop-up device protrudes outward from the electronic device and including a plurality of first terminals formed on an outer surface of the pop-up device to be electrically connected to an external device; a power supplier configured to supply electric power to the gas sensor; a clock generator configured to generate a clock signal that is used in a gas sensing operation of the gas sensor; a first conductive line electrically connected to the power supplier; and a second conductive line electrically connected to the clock generator, wherein connections between the first conductive line and the second conductive line, and the plurality of first terminals of the pop-up device, are disconnected when the pop-up device is in the inserted state, and the first conductive line and the second conductive line are physically connected to the plurality of first terminals when the pop-up device is in the pop-up state.

According to some example embodiments of the inventive concepts, there is provided a method of operating an electronic device, the electronic device including a pop-up device configured to be inserted into a main body of the electronic device in an inserted state of the pop-up device, the pop-up device comprising a gas sensor configured to be exposed at least partially to an outer portion of the electronic device in a pop-up state of the pop-up device in which at least a part of the pop-up device protrudes outward from the electronic device, the method including: determining whether the pop-up device is in the pop-up state or the inserted state; in response to determining that the pop-up device is in the pop-up state, supplying electric power and a clock signal to the gas sensor mounted in the pop-up device from a circuit arranged on the outer portion of the pop-up device, and outputting sensing information indicating a gas sensing result to the circuit on the outer portion of the pop-up device; and in response to determining that the pop-up device is in the inserted state, blocking supply of the electric power and the clock signal to the gas sensor mounted in the pop-up device.

BRIEF DESCRIPTION OF THE DRAWINGS

Example embodiments of the inventive concepts will be more clearly understood from the following detailed description taken in conjunction with the accompanying drawings in which.

DETAILED DESCRIPTION

Hereinafter, some example embodiments of the inventive concepts will be described in detail with reference to accompanying drawings. Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particular manner, a function or operation specified in a specific block may be performed differently from the flow specified in a flowchart, flow diagram, etc. For example, functions or operations illustrated as being performed serially in two consecutive blocks may actually be performed concurrently, simultaneously, or in some cases be performed in reverse order.

Figure 1:
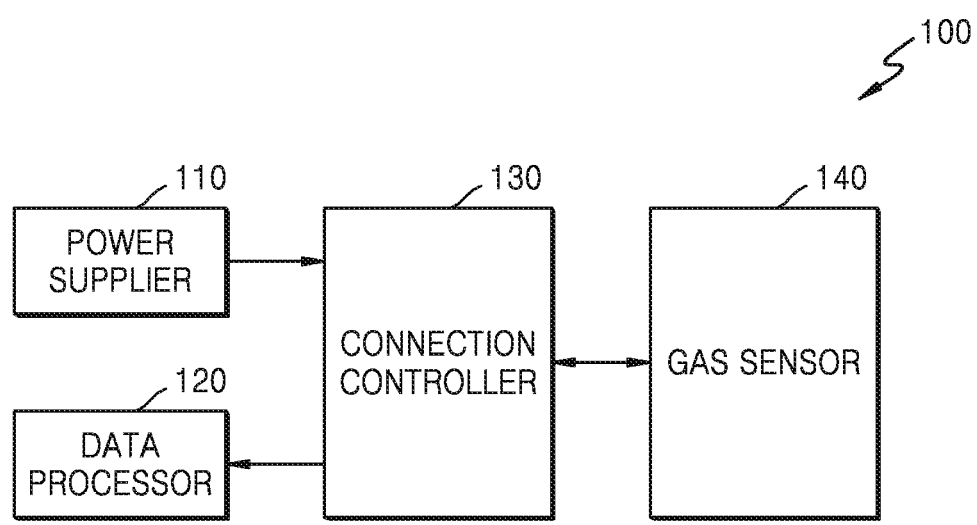
FIG. 1 is a block diagram of an electronic device including a gas sensor according to some example embodiments.

FIG. 1 is a block diagram of an electronic device 100 including a gas sensor according to some example embodiments. The electronic device 100 of FIG. 1 shows configurations related to an operation of a gas sensor according to some example embodiments, and thus, the electronic device 100 of FIG. 1 may be also referred to as a gas sensing system. In addition, the gas sensing system may be referred to as an electronic nose system.

The electronic device 100 may include a power supplier 110, a data processor 120, a connection controller 130, and a gas sensor 140. The power supplier 110 may supply electric power to the gas sensor 140, or may block the supply of electric power to the gas sensor 140, according to a connection state of the connection controller 130. In addition, the gas sensor 140 may include a sensor block (not shown) configured to be exposed to the outside as a pop-up from a state of being located inside the electronic device 100 so as to contact actual gas or smell (hereinafter, various materials that may be sensed by the gas sensor 140 are referred to as 'gas'), and sensing information indicating a result of sensing the gas by using the sensor block may be provided from the gas sensor 140 to the data processor 120. Here, the sensing information may be provided to the data processor 120, or the providing of the sensing information to the data processor 120 may be blocked (disabled or prevented), according to the connection state of the connection controller 130.

The data processor 120 may perform various processing operations by using the sensing information as data (e.g., input data). For example, the sensing information may be processed to display the gas sensing result through a display (not shown) of the electronic device 100 or to generate an output for generating a notification. Alternately, the data processor 120 may be connected to other various kinds of sensors included in the electronic device 100 and may perform a data processing operation after combining sensing information from a plurality of sensors to generate data in which sensing results of the various kinds of sensors are combined. That is, the data processor 120 may perform various kinds of processing operations by using the sensing information generated in the electronic device 100, and output data from the data processor 120 may be provided to other elements (e.g., an application processor) in the electronic device 100 and/or to another external device on an outer portion of the electronic device 100.

The gas sensor 140 may include a sensor block in which various kinds of sensors are arranged. As a non-limiting example, the sensor block may include a film bulk acoustic resonator (FBAR) sensor for sensing one or more kinds of gases. Each of the FBAR sensors includes the FBAR as a resonator, and at the same time, may include a sensing layer (e.g., polymer) coated on the FBAR. Also, in order to sense various kinds of gases, the FBAR sensors may be coated with different sensing layers that may combine with different kinds of gases to change the resonant characteristics of the FBAR sensors.

In addition, according to some example embodiments, the sensor block may include various kinds of resonators, for example, the sensor block may include a bulk acoustic wave (BAW) resonator, a surface acoustic wave (SAW) resonator, a solidly mounted resonator (SMR), etc.

As a non-limiting example, the gas sensor 140 may include an oscillator block (not shown) that outputs an oscillating signal having a frequency corresponding to the resonant frequency of the FBAR sensors, together with the sensor block including the FBAR sensors. According to some example embodiments, the oscillator block may include a plurality of oscillators, each of which may generate an oscillating signal corresponding to the resonant frequency of a corresponding FBAR sensor, and the frequency of the oscillating signal from the oscillator may vary when the resonant frequency of the FBAR sensor is changed according to a result of sensing gas. Also, the gas sensor 140 may further include a sensing logic (not shown), and the sensing logic detects the frequency of the oscillating signal and generates sensing information based on the detected frequency. As a non-limiting example, when the sensing information is generated based on counting of the frequency of the oscillating signal by the sensing logic, the sensing logic may be also referred to as a frequency counting logic.

In order to prevent (limit or reduce) contamination of the FBAR sensors due to long-time exposure to the outside, the gas sensor 140 may be configured to be inserted into the electronic device 100, and to be exposed to the outer portion of the electronic device 100 only if necessary (e.g., only when the gas sensing is to be performed). For example, the gas sensor 140 may pop up when a push button (not shown) of the electronic device 100 is pushed. For example, the gas sensor 140 may be mounted in a pop-up device (e.g., in the form of a slim rod type device such as a stylus pen), and a power supply device and a clock generator that enable the gas sensing operation of the gas sensor 140 to be performed and/or a data processing logic and a communication device for processing the sensing information may be provided on an outer portion of the pop-up device in the electronic device 100. Also, the gas sensor 140 may selectively receive a power supply and a clock signal during an actual gas sensing operation. As used herein, the terms "the outside" or "the outer portion of the electronic device" may refer to the gas sensor 140 of the pop-up device being exposed to the open air, atmosphere, external environment, etc. surrounding the electronic device 100.

The connection controller 130 may have a connecting control state for controlling supply of electric power to the gas sensor 140 and/or controlling transfer of the sensing information from the gas sensor 140. As a non-limiting example, the transferring of the electric power and the sensing information may be allowed (enabled) or blocked (disabled or prevented) according to a location of the pop-up device, in which the gas sensor 140 is mounted, in relation to the electronic device 100. In FIG. 1, the connection controller 130 is shown as an additional element, but some other example embodiments are not limited thereto. For example, the connection controller 130 may include conductive lines and terminals (or pads) for transferring the electric power and the sensing information. According to some example embodiments, a first set of the conductive lines and terminals may be arranged in the power supplier 110 and the data processor 120, and a second set of the conductive lines and terminals may be formed in (or on an outer portion of) the pop-up device including the gas sensor 140.

Also, a connection state between the power supplier 110 and the data processor 120, and the gas sensor 140, may be controlled in various ways. For example, the electric power and the sensing information may be transferred through physical contact with the conductive lines and terminals, or the electric power and the sensing information may be transferred in contactless ways (e.g., an electromagnetic way) between the power supplier 110 and the data processor 120, and the gas sensor 140.

In addition, selective transfer of the electric power and the sensing information according to the connection control state of the connection controller 130 may be selected in various ways. For example, as the pop-up device in which the gas sensor 140 is mounted moves (e.g., from being located inside the electronic device 100 to the pop-up state, or from the pop-up state to the inserted state), the conductive lines or terminals formed on the pop-up device also move, and accordingly, the conductive lines and terminals may be mechanically connected or disconnected. Alternately, a pop-up determination circuit (a circuit capable of determining a pop-up state of the pop-up device) for determining a location of the pop-up device, in which the gas sensor 140 is mounted, in relation to the electronic device 100 may be provided in the electronic device 100, the conductive lines and terminals are connected to each other via switches, and then, the conductive lines and terminals may be connected to or disconnected from each other based on controlling of the switches by the pop-up determination circuit.

In addition, the pop-up device in which the gas sensor 140 is mounted may be completely separated from the electronic device 100 according to manipulation of a user. For example, the electric power is supplied to the gas sensor 140 in the pop-up state of the pop-up device (e.g., when the pop-up device moves from being located inside the electronic device 100 to the pop-up state, such that a portion of the pop-up device protrudes outward from the electronic device, but the remaining portion of the pop-up device remains inside the electronic device such that the pop-up device is not completely separated from the electronic device 100), and then, the supply of the electric power to the gas sensor 140 may be blocked (disabled or prevented) when the pop-up device is completely separated from the electronic device 100 (e.g., removed from the electronic device 100 by the user). According to some example embodiments, since the gas sensor 140 may be separated from the electronic device 100 via removal of the pop-up device, when the performance of the gas sensor 140 degrades (e.g., when gas sensing accuracy and/or sensitivity has reduced due to contamination of the gas sensor 140) and/or the gas sensor 140 reaches the end of the lifespan thereof, the gas sensor 140 may be easily replaced by replacing the pop-up device (e.g., by replacing the stylus pen or other similar form factor in which the gas sensor 140 is mounted).

In addition, although FIG. 1 only shows a configuration of controlling the supply of the electric power to the gas sensor 140 for convenience of description, some other example embodiments are not limited thereto. For example, various kinds of signals that can drive the gas sensor 140, for example, a clock signal, a control signal, etc., may be supplied or not be supplied to the gas sensor 140 according to the connection state of the connection controller 130.

Figure 2:
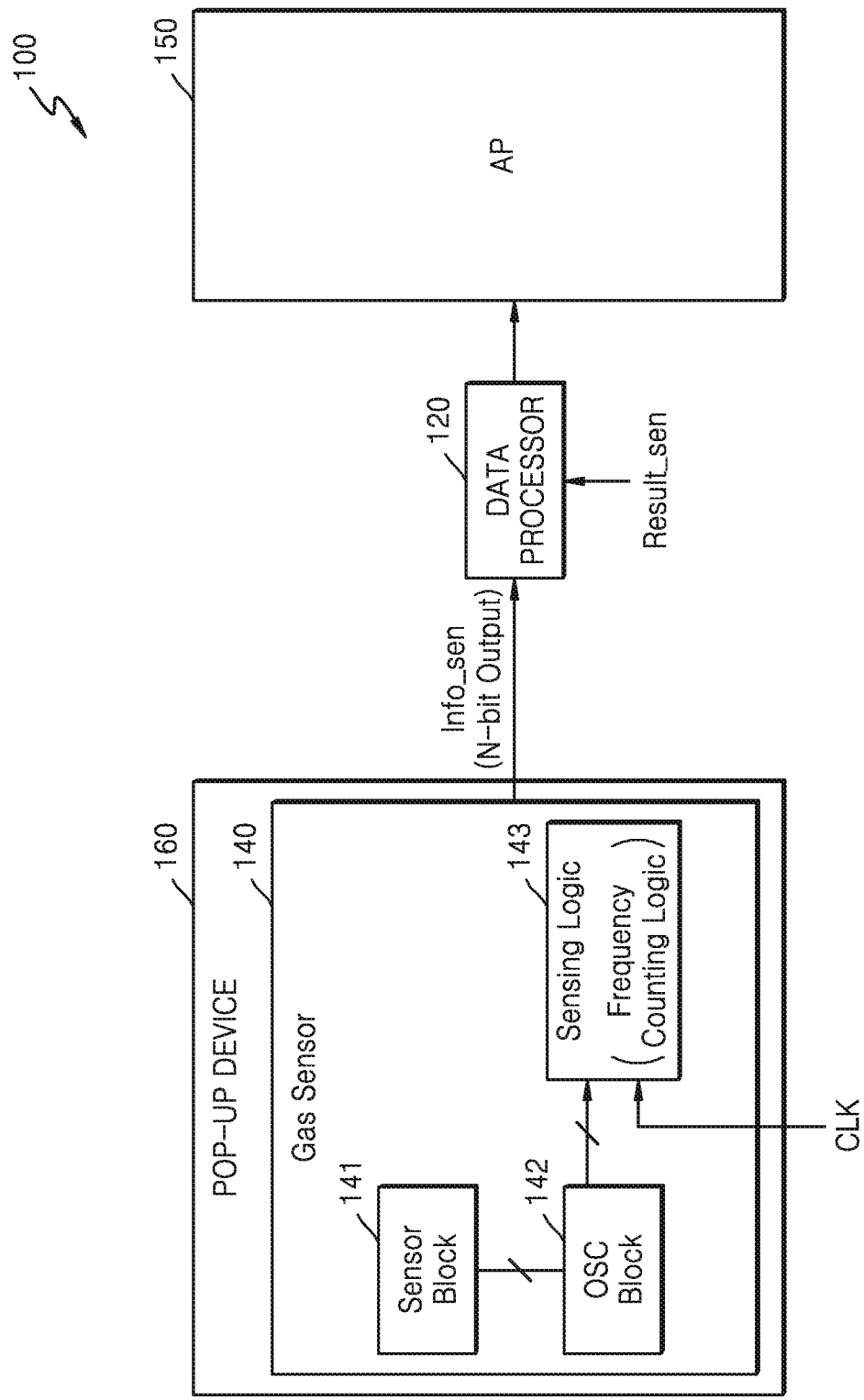
FIG. 2 is a block diagram of an example of implementing a gas sensor in an electronic device according to some example embodiments.

FIG. 2 is a block diagram of an example of implementing the gas sensor 140 in an electronic device according to some example embodiments. FIG. 2 further shows an application processor (AP) 150 that controls overall operations of the electronic device 100 and may be implemented as a system-on-chip according to some example embodiments, and further shows a pop-up device 160, in which the gas sensor 140 is mounted.

Referring to FIG. 1 and FIG. 2, the gas sensor 140 mounted in the pop-up device 160 may include a sensor block 141, an oscillator block (OSC) 142, and a sensing logic 143. Also, as described above, when the sensing logic 143 outputs sensing information Info_sen based on counting of a frequency of the oscillating signal from the oscillator block 142, the sensing logic 143 may be referred to as a frequency counting logic. The sensor block 141 may include a plurality of FBAR sensors based on the FBAR, and the sensing logic 143 may count the frequency of the oscillating signal based on a clock signal CLK provided from the outside of the pop-up device 160 and generate the sensing information Info_sen based on a counting result.

According to some example embodiments, the sensing logic 143 may count edges (e.g., rising edges and/or falling edges) in each of a plurality of oscillating signals in a period (e.g., logic low or logic high) during which the clock signal CLK has a certain state. For example, the sensing information Info_sen may correspond to a digital code (N-bit output) having a predetermined (or desired) number of bits.

The sensing information Info_sen having the digital code (N-bit output) may be provided to the data processor 120, and the data processor 120 may perform data processing on the sensing information Info_sen from the gas sensor 140 to generate and output a processing result (a gas sensing result) to the application processor 150. According to some example embodiments, the data processor 120 may receive a sensing result Result_sen from one or more different kinds of sensors included in the electronic device 100 and may further perform a data processing operation using the sensing result Result_sen. For example, the data processor 120 may perform the data processing on the sending information Info_sen from the gas sensor 140 in combination with the sensing result Result_sen from the one or more different kinds of sensors to generate the processing result (the gas sensing result). The application processor 150 receives the gas sensing result through the data processor 120 and may output the gas sensing result to a display (not shown) of the electronic device 100, or may control various operations such as an LED notification, a voice output, etc., as a post-process using the gas sensing result according to some example embodiments.

According to some example embodiments, the gas sensor 140 may be implemented in various types. For example, the gas sensor 140 may correspond to one semiconductor chip, in which various elements included in the gas sensor 140 may be implemented on a wafer. Alternatively, according to some other example embodiments, the gas sensor 140 may include at least two semiconductor chips. For example, the sensor block 141 including one or more sensors (e.g., FBAR sensors) may be implemented as a separate chip, the oscillator block 142 and the sensing logic 143 may be implemented as one semiconductor chip, and the sensor block 141 and the oscillator block 142 may be electrically connected to each other via a conductive line, such as a bonding wire, for example.

As a modified example embodiment, an additional process using the digital code (N-bit output) corresponding to the sensing information Info_sen may be performed in the gas sensor 140. For example, at least some of the data processing functions of the data processor 120 may be executed in the gas sensor 140.

In addition, the electronic device 100 according to some example embodiments may include at least one of, for example, a smartphone, a tablet personal computer (PC), a mobile phone, a video phone, an e-book reader, a laptop, a netbook computer, a personal digital assistant (PDA), a portable multimedia player (PMP), an MP3 player, a mobile medical appliance, a camera, an electronic appliance, a device for a vehicle, and a wearable device. According to some example embodiments, a wearable device may be implemented as an accessory (e.g., a watch, a ring, a wristlet, a necklace, glasses, contact lenses, or a head-mounted device (HMD)) that may be worn by a user.

Figure 3:
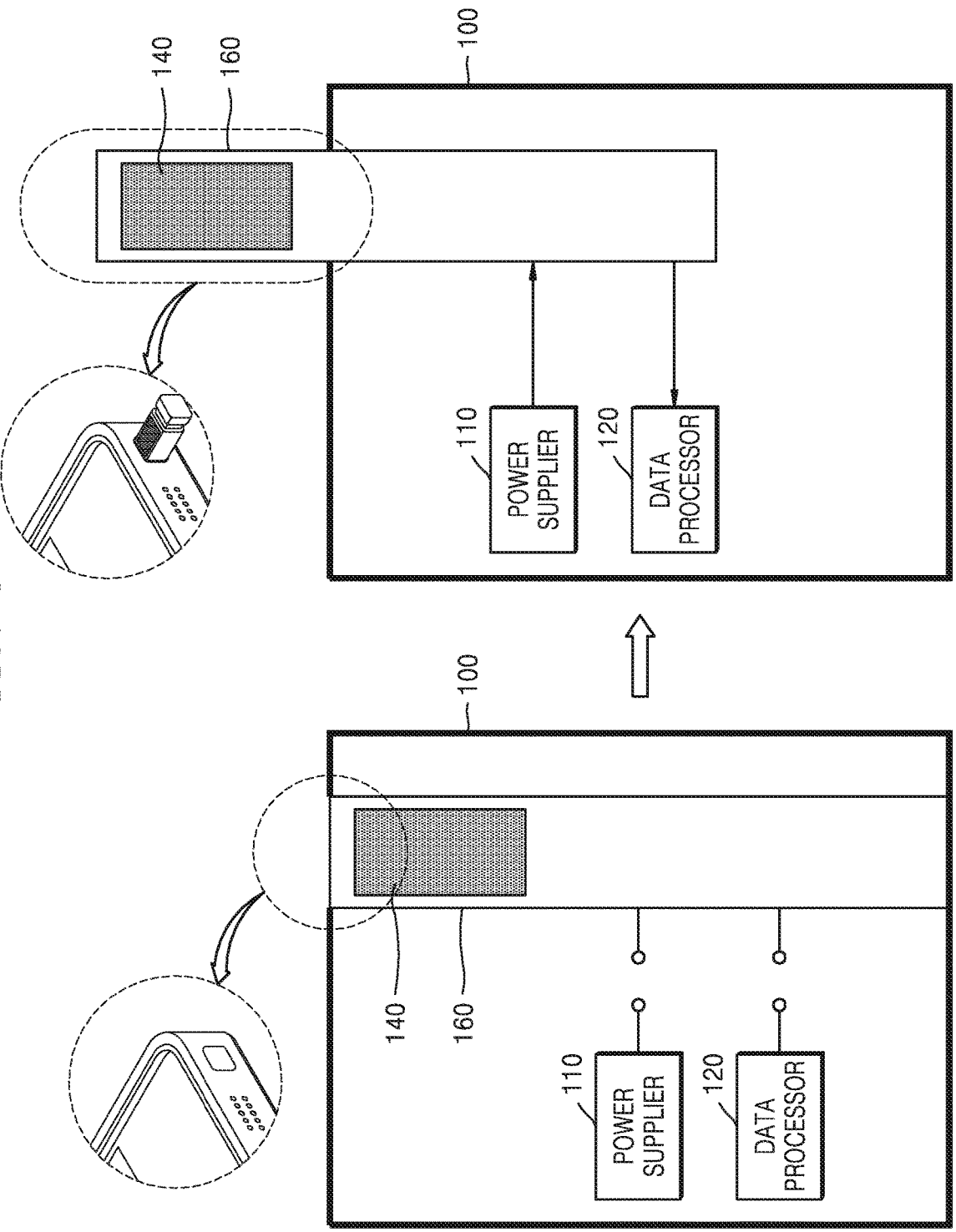
FIG. 3 is a block diagram showing an example of a connection state according to a location of a pop-up device in relation to an electronic device according to some example embodiments.

FIG. 3 is a block diagram showing an example of a connection state according to a location of the pop-up device 160 in relation to the electronic device 100 according to some example embodiments.

Referring to FIG. 1 to FIG. 3, connection states of various signals and electric power with respect to the gas sensor 140 may be controlled according to whether the pop-up device 160 is inserted in the electronic device 100 (inserted state), or at least a part of the pop-up device 160 protrudes out of the electronic device 100 (pop-up state). For example, as shown on the left of FIG. 3, when the pop-up device 160 is inserted into the main body of the electronic device 100 (inserted state), a connection between the power supplier 110 and the gas sensor 140 is blocked (disconnected or disabled), and accordingly, supply of electric power to the gas sensor 140 may be blocked (disabled or prevented). Also, since electric power is not supplied to the gas sensor 140, a gas sensing operation may not be performed, and accordingly, the gas sensor 140 may not perform an operation of generating and outputting the sensing information Info_sen. In addition, since a connection between the gas sensor 140 and the data processor 120 is blocked (disconnected or disabled), communication between the gas sensor 140 and the data processor 120 may be blocked (disabled or prevented).

On the other hand, as shown on the right of FIG. 3, when a portion of the pop-up device 160 protrudes outward from the electronic device 100 (pop-up state), the sensor block 141 included in the gas sensor 140 may be exposed to the outside (the outer portion of the electronic device 100), the connections between the power supplier 110 and the data processor 120, and the gas sensor 140, are connected (enabled), and accordingly, the electric power for operating the gas sensor 140 is supplied to the gas sensor 140, and the sensing information Info_sen from the gas sensor 140 may be provided to the data processor 120. As described above, the connection controller 130 included in the electronic device 100 may control the supply of electric power from the power supplier 110 to the gas sensor 140 through a contact-type connection control or a contactless-type connection control according to the location of the pop-up device 160 in relation to the electronic device 100 (that is, whether the pop-up device 160 is in the inserted state or the pop-up state with respect to the electronic device 100).

In addition, FIG. 3 further shows perspective views showing the pop-up device 160 in the inserted state, in which the pop-up device 160 is located inside the electronic device 100 (left side of FIG. 3), and in the pop-up state, in which a part of the pop-up device 160 having at least the gas sensor 140 mounted therein protrudes outward from the electronic device 100 (right side of FIG. 3). Also, the pop-up device 160 shown in the perspective view may be implemented in the form of a stylus pen, for example, which is insertable into the electronic device 100 and removable from the electronic device 100.

Referring to the example embodiments described above with reference to FIGS. 1, 2, and 3, the pop-up device 160 having the gas sensor 140 mounted therein provides various technological improvements or technical advantages over the conventional art. Because the gas sensor 140 is usually located inside the electronic device 100 in the inserted state and may only be exposed to the outside in the pop-up state when the gas sensing operation needs to be performed, the contamination and resulting performance degradation may be prevented (limited or reduced) thereby increasing the usable lifespan of the gas sensor, as compared to the conventional related art. Furthermore, by providing a mechanism (e.g., the connection controller 130) for controlling the connection state between the components of the electronic device 100 (e.g., the power supplier 110, the data processor 120, etc.) and the gas sensor 140 of the pop-up device 160, the supply of electric power to the gas sensor 140 can be managed based on the connection state, thereby reducing the amount of electric power consumed to perform the gas sensing operations and sensing information communication operations. In addition, by mounting the gas sensor 140 in a form factor such as a stylus pen, mobile devices such as smartphones, etc. can be easily equipped with a gas sensor, which can be replaced simply by replacing the stylus pen, such as when the gas sensor becomes contaminated, when performance (accuracy, sensitivity, etc.) degrades, and/or when the gas sensor has reached (or is nearing) the end of its lifespan.

Figure 4A:
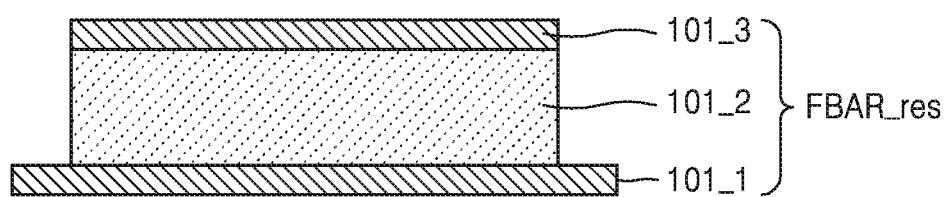
FIGS. 4A and 4B are diagrams showing examples of a film bulk acoustic resonator (FBAR) sensor.
Figure 4B:
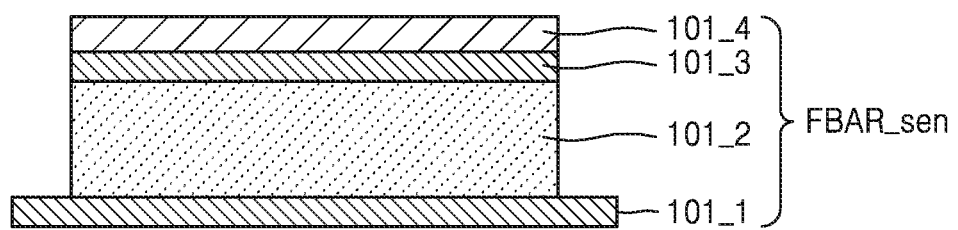

FIGS. 4A and 4B are diagrams showing examples of a film bulk acoustic resonator (FBAR) sensor. FIG. 4A shows an example of a resonator based on FBAR, and FIG. 4B shows an example of an FBAR sensor using the resonator based on FBAR. FIGS. 4A and 4B each show one FBAR sensor, but the sensor block may include a plurality of FBAR sensors according to some other example embodiments.

Referring to FIG. 4A, an FBAR resonator FBAR_res may have a structure, in which a lower electrode 101_1, a piezoelectric layer 101_2, and an upper electrode 101_3 are sequentially stacked. The piezoelectric layer 101_2 may include a thin film and may include zinc oxide (ZnO), aluminum nitride (AlN), lead zirconate titanate (PZT), or other various kinds of piezoelectric materials. A resonant frequency of the FBAR may be determined according to a thickness of the piezoelectric layer 101_2, and when a radio frequency (RF) voltage corresponding to the resonant frequency is applied to the lower electrode 101_1 and the upper electrode 101_3, the FBAR resonator FBAR_res may resonate in a direction in which the lower and upper electrodes 101_1 and 101_3 and the piezoelectric layer 101_2 are stacked.

Although not shown in FIG. 4A for the convenience of description, the FBAR may be formed on a substrate including silicon or glass, and an insulating layer including $SiO_2$, etc. may be arranged between the FBAR and the substrate.

In addition, FIG. 4B shows an example of implementing an FBAR sensor FBAR_sen, and as shown in FIG. 4B, the FBAR sensor FBAR_sen may include the lower and upper electrodes 101_1 and 101_3 and the piezoelectric layer 101_2 included in the FBAR resonator FBAR_res, and a sensing layer 101_4 may be coated on the FBAR resonator FBAR_res for sensing or measuring odor or gas. When molecules of the gas, etc. are sensed by the FBAR sensor FBAR_sen, the resonant frequency of the FBAR resonator FBAR_res is changed, and the frequency of the oscillating signal output from the oscillator block 142 is also changed. The gas may be sensed or measured by detecting the frequency of the oscillating signal. In addition, the FBAR sensor FBAR_sen of FIG. 4B may be used as various kinds of sensors such as a mass airflow sensor, an Internet of things (IoT) sensor, etc.

A receptor of the sensing layer 101_4 may include various kinds of materials, and according to some example embodiments, the resonant frequency of the FBAR resonator FBAR_res may vary depending on a kind of gas sensed by the materials included in the sensing layer 101_4. Also, according to some example embodiments, the resonant frequency of the FBAR resonator FBAR_res may vary depending on a concentration of the gas sensed by the sensing layer 101_4. For example, the sensing layer 101_4 may include a polymer, and a polymer corresponding to various kinds of gases to be sensed is implemented and coated on the FBAR resonator FBAR_res such that the FBAR sensors FBAR_sen capable of sensing various gases may be implemented.

Figure 5:
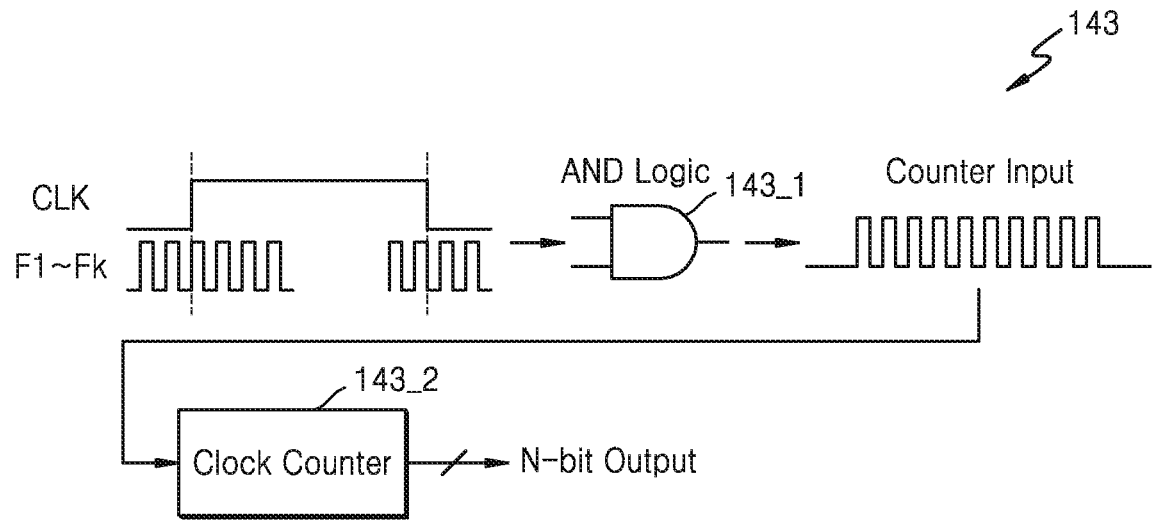
FIG. 5 is a block diagram showing an example of a sensing logic of FIG. 2.

FIG. 5 is a block diagram showing an example of the sensing logic 143 of FIG. 2.

Referring to FIG. 1 to FIG. 5, the oscillator block 142 may include a plurality of oscillators arranged to respectively correspond to the plurality of FBAR sensors, and oscillating signals F1 to Fk from the plurality of oscillators may be provided to the sensing logic 143. The oscillating signals F1 to Fk may have frequencies that vary depending on gas sensing results of the plurality of FBAR sensors.

The sensing logic 143 may include one or more logic devices and one or more counters. As a non-limiting example, the sensing logic 143 may include a logic device 143_1 performing a calculating process on the clock signal CLK and each of the oscillating signals F1 to Fk. For example, the logic device 143_1 may include an AND logic performing an AND operation on the clock signal CLK and the oscillating signals F1 to Fk. Also, the sensing logic 143 may further include a clock counter 143_2, and the clock counter 143_2 may count a clock of a signal output from the logic device 143_1 (counter input) to generate a sensing result (N-bit output) as the sensing information Info_sen. As a non-limiting example, FIG. 5 shows a case in which the sensing logic 143 is shared by a plurality of oscillators, but the sensing logic 143 may be arranged to correspond to each of the oscillators according to some other example embodiments.

For example, a first oscillator corresponding to a certain FBAR sensor (e.g., a first FBAR sensor) may output a first oscillating signal F1 having a frequency difference $\Delta F$ between a case in which the gas is sensed and a case in which the gas is not sensed. Also, the value of $\Delta F$ corresponding to the frequency difference may vary depending on a concentration of the sensed gas. The logic device 143_1 may perform an AND operation on the clock signal CLK and the first oscillating signal F1 and may output a signal, toggling of which is activated, while the clock signal CLK has a logic high H state. An output from the logic device 143_1 is provided as a counter input of the clock counter 143_2, and a frequency of the clock signal in a section where the toggling of the counter input is activated may correspond to the frequency of the first oscillating signal F1.

The clock counter 143_2 may receive the counter input corresponding to the output of the logic device 143_1 and may count the number of rising edges and/or falling edges of the clock signal. A digital code (N-bit output) having a predetermined (or desired) number of bits may be generated according to a result of counting the number of edges, and the digital code (N-bit output) may be output as the sensing information Info_sen. The counting may be performed in various ways. For example, in FIG. 5, it is shown that the clock is counted in one cycle of the clock signal CLK, but the clock may be counted within two or more cycles of the clock signal CLK according to some other example embodiments. Also, in the above-described example embodiment, both the rising edges and the falling edges of the clock signal are counted, but only one of the rising edges or the falling edges of the clock signal may be counted according to some other example embodiments.

Figure 6:
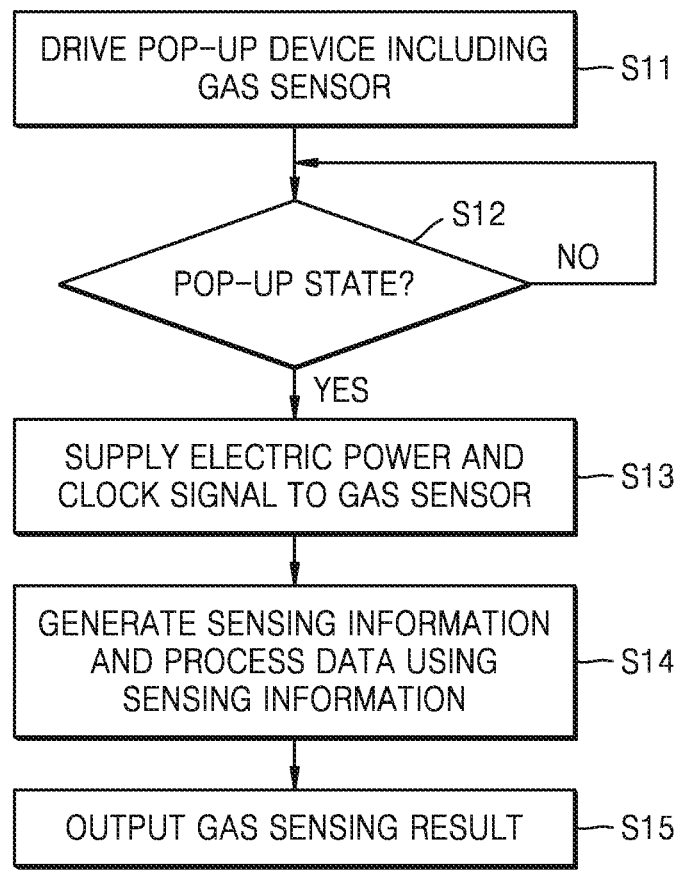
FIG. 6 is a flowchart illustrating a method of operating an electronic device, according to some example embodiments.

FIG. 6 is a flowchart illustrating a method of operating an electronic device, according to some example embodiments. As a non-limiting example, the flowchart of FIG. 6 may correspond to a gas sensing method of an electronic device including a gas sensor.

Referring to FIG. 6, the electronic device may include a pop-up device, at least a part of which may protrude outward from the electronic device so as to be exposed to the outside according to manipulation of a user (pop-up state), and the gas sensor according to some example embodiments may be mounted in the pop-up device. The pop-up device may be driven to be inserted into a main body of the electronic device (inserted state) or to be in the pop-up state according to manipulation of a user (S11). According to some example embodiments, a connection controller of the electronic device (or a pop-up determination circuit) may determine a state of the pop-up device in relation to the electronic device (that is, the connection controller or the pop-up determination circuit may determine a location of the pop-up device with respect to the electronic device). For example, the connection controller or the pop-up determination circuit may determine whether the pop-up device is in the inserted state, in which the pop-up device is inserted into the main body of the electronic device, or in the pop-up state, in which a part of the pop-up device that includes a sensor block (or FBAR sensor) included in the gas sensor is exposed to the outside of the electronic device (S12).

According to a determination result at S12, supplying of electric power and various signals to the gas sensor may be controlled. For example, when the connection controller or the pop-up determination circuit determines that the pop-up device is in the inserted state (No at S12), the supply of the electric power and signals to the gas sensor is blocked (disabled or prevented) while the pop-up device is inserted into the main body of the electronic device. On the other hand, when the connection controller or the pop-up determination circuit determines that the pop-up device is in the pop-up state (Yes at S12), the electric power and a clock signal used in the gas sensing operation may be allowed (enabled) to be supplied to the gas sensor (S13). Also, since the pop-up device is in the pop-up state, communication between the gas sensor and a data processor on an outer portion of the pop-up device is activated (or enabled), and accordingly, the gas sensor may generate sensing information and the data processor may perform data processing by using the sensing information (S14). A gas sensing result is generated and may be used in the electronic device, or may be provided to another external device on an outer portion of the electronic device. For example, the gas sensing result may be displayed on a display of the electronic device and/or may be output in various ways such as LED notification, voice notification, etc. (S15).

Figure 7A:
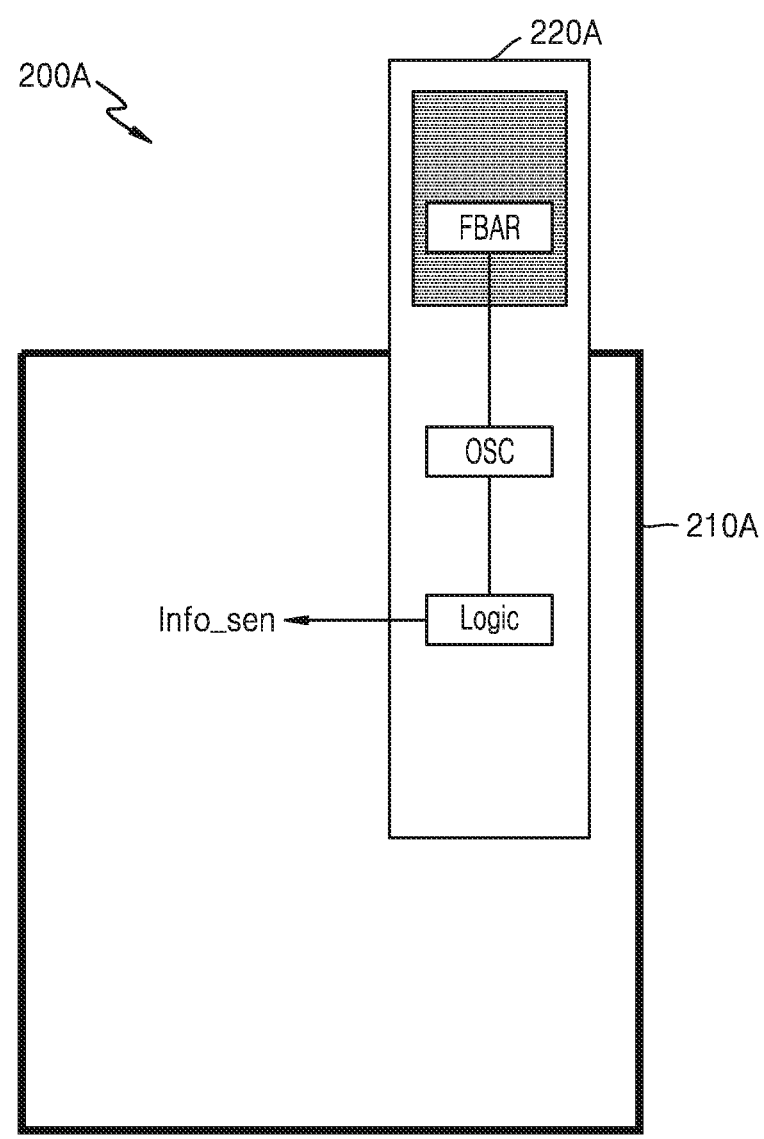
FIGS. 7A and 7B are block diagrams showing various implementations of an electronic device according to some example embodiments.
Figure 7B:
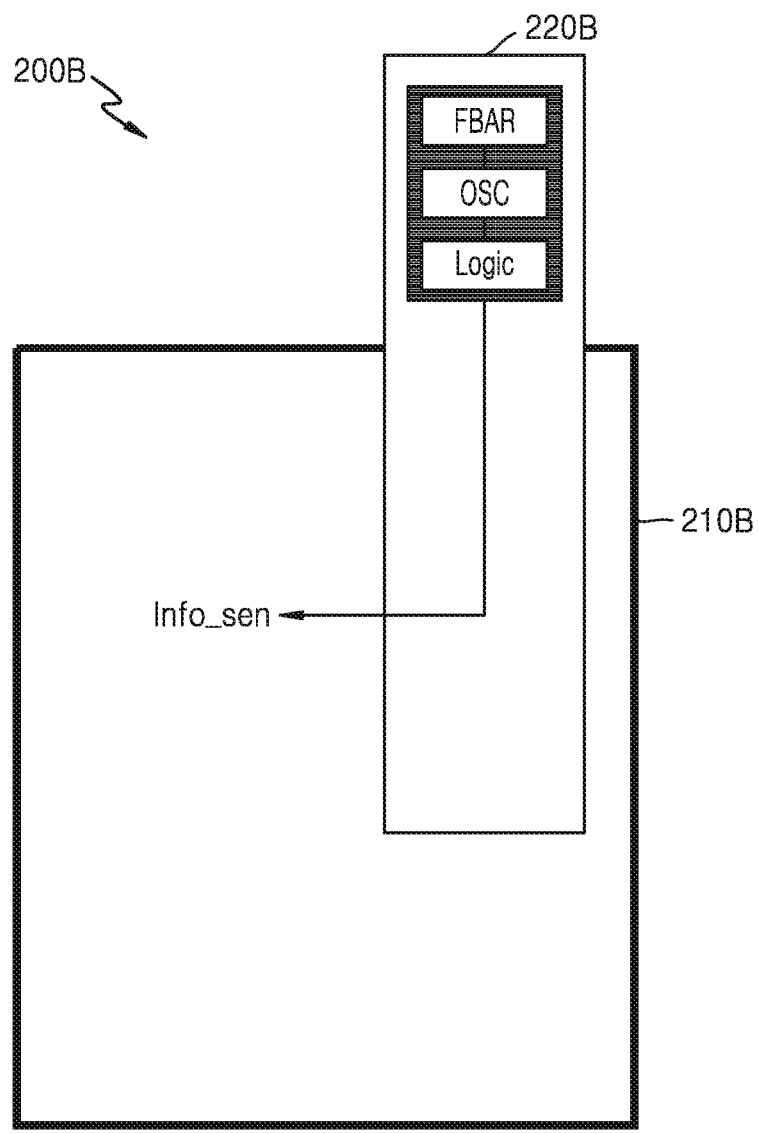

FIGS. 7A and 7B are block diagrams showing various implementations of an electronic device 200A according to some example embodiments.

Referring to FIG. 7A, the electronic device 200A includes a pop-up device 220A that may be inserted into a main body 210A of the electronic device 200A, and a gas sensor mounted in the pop-up device 220A may include a film bulk acoustic resonator sensor block FBAR. The pop-up device 220A may also include an oscillator block OSC and a sensing logic Logic, and the sensing logic Logic may output sensing information Info_sen according to a gas sensing result generated by the sensing logic Logic.

When the pop-up device 220A is in the pop-up state, only some of the components included in the gas sensor may be exposed to the outside (the outer portion) of the electronic device 200A. For example, the sensor block FBAR is exposed to the outer portion of the electronic device 200A in the pop-up state, but the oscillator block OSC and the sensing logic Logic may remain located inside the main body 210A in the pop-up state. For example, only the sensor block FBAR, which is coated with a sensing material, may be exposed to the outer portion of the electronic device 200A in order to sense the external gas, and the gas sensor may be mounted in the pop-up device 220A as shown in FIG. 7A (e.g., the shaded area in FIG. 7A).

For example, the sensor block FBAR and the oscillator block OSC may be connected to each other via a conductive line (not shown), and the oscillator block OSC may generate an oscillating signal having a frequency corresponding to a resonant frequency of the sensor block FBAR. However, as a distance between the sensor block FBAR and the oscillator block OSC increases, a length of the conductive line also increases, and thus spurious resonance may occur due to a parasitic capacitance component, a parasitic inductance component, etc. of the conductive line. That is, when the spurious resonance occurs, the oscillator block OSC may oscillate at an unintended frequency, which may degrade the performance of the gas sensor. Therefore, the electronic device 200B of FIG. 7B may be provided to address the spurious resonance issue, according to some other example embodiments.

Referring to FIG. 7B, the electronic device 200B includes a pop-up device 220B that may be inserted into a main body 210B of the electronic device 200B, and a gas sensor mounted in the pop-up device 220B may include a sensor block FBAR, an oscillator block OSC, and a sensing logic Logic.

When the pop-up device 220B is in the pop-up state, the sensor block FBAR, the oscillator block OSC, and the sensing logic Logic included in the gas sensor are all exposed to the outside (the outer portion) of the electronic device 200B. In order to prevent (limit or reduce) generation of the spurious resonance, the gas sensor may be mounted in the pop-up device 220B as shown in FIG. 7B (e.g., the shaded area in FIG. 7B) so that the oscillator block OSC may be exposed to the outer portion of the electronic device 200B together with the sensor block FBAR, and the length of the conductive line connecting the sensor block FBAR and the oscillator block OSC may be reduced (e.g., as compared to FIG. 7A). Thus, the configuration of components in the pop-up device 220B of FIG. 7B may prevent (limit or reduce) the degradation of performance of the gas sensor due to spurious resonance, as compared to the configuration of components in the pop-up device 220A of FIG. 7A.

Figure 8A:
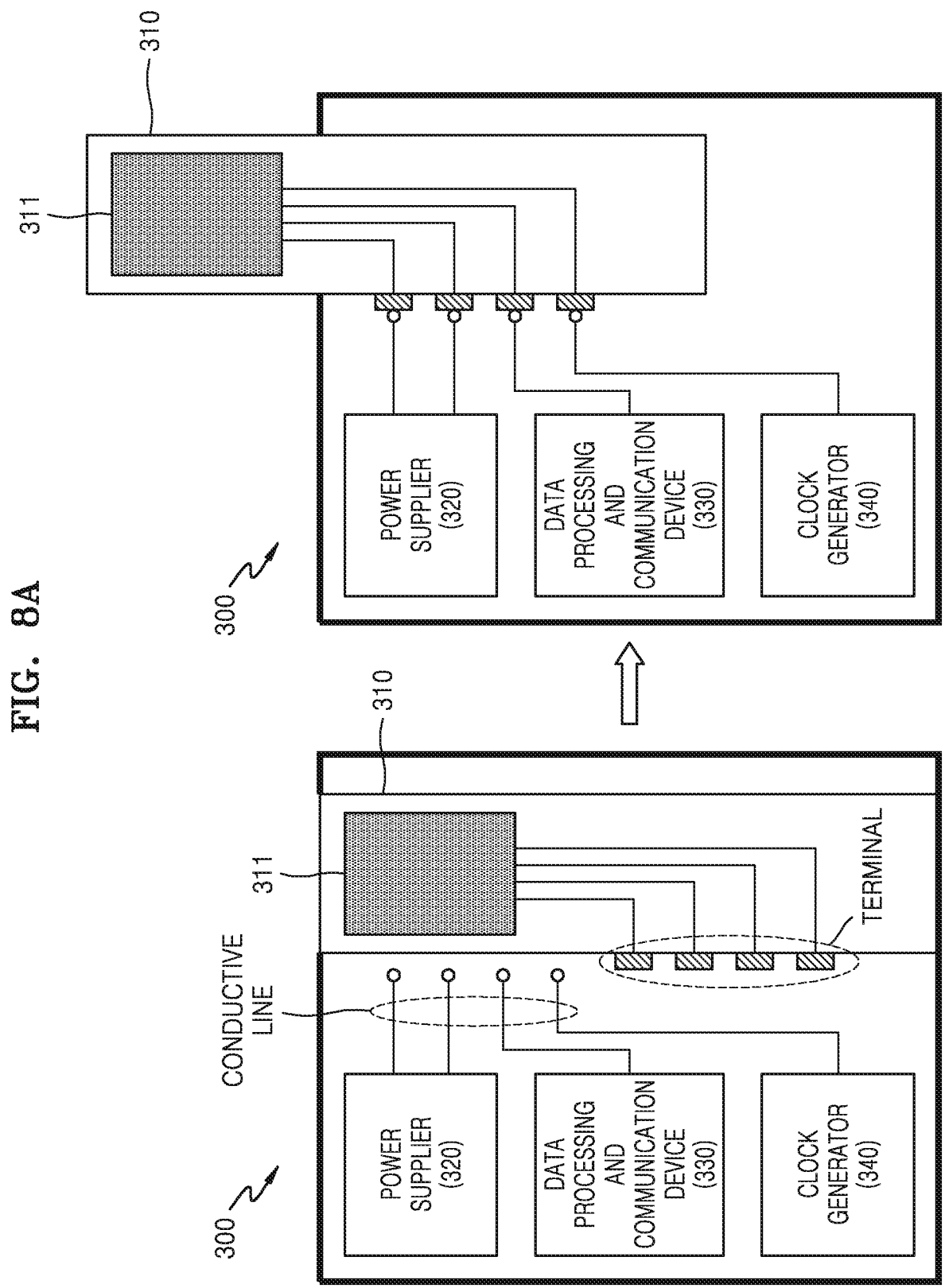
FIGS. 8A and 8B are block diagrams showing various implementations of an electronic device according to some example embodiments.
Figure 8B:
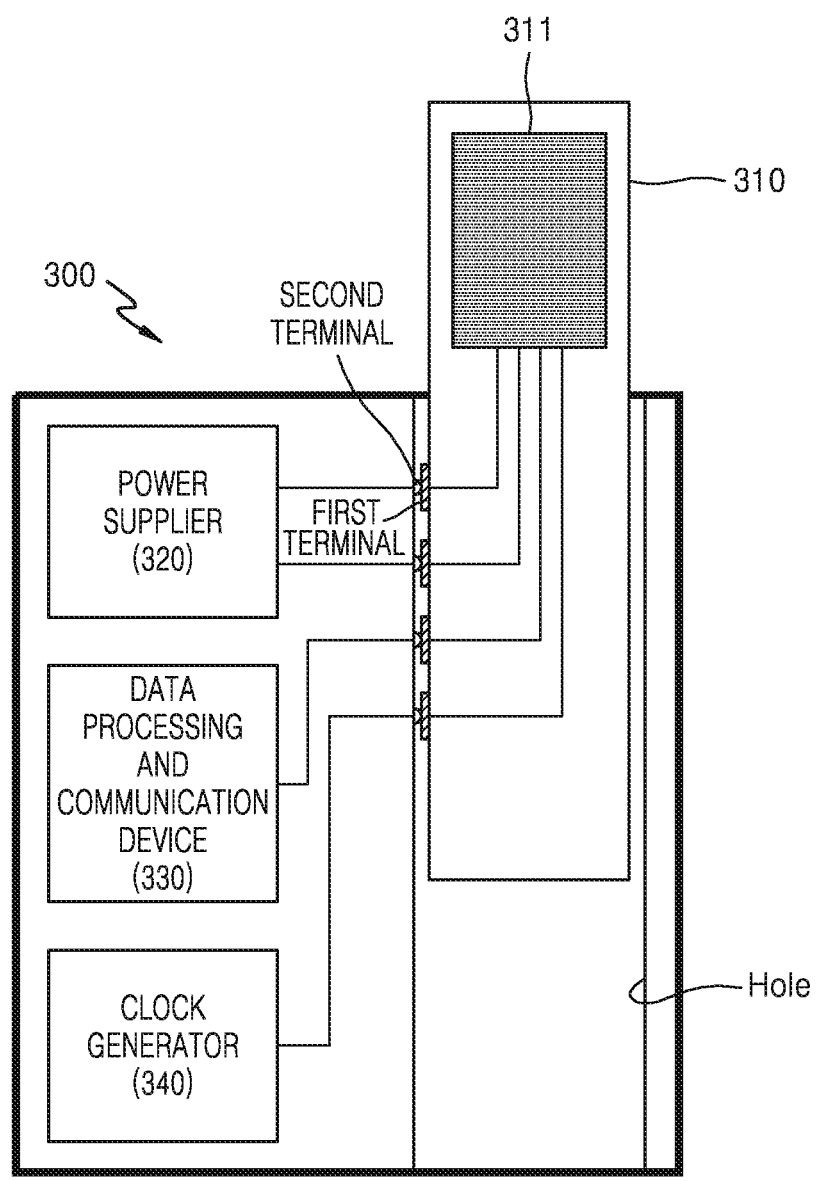

FIGS. 8A and 8B are block diagrams showing various implementations of an electronic device 300 according to some example embodiments.

Referring to FIG. 8A, the electronic device 300 includes a pop-up device 310, a power supplier 320, a data processing and communication device 330, and a clock generator 340, and the pop-up device 310 may include a gas sensor 311, according to some example embodiments. Also, the power supplier 320 may be the component for supplying the electric power to the gas sensor 311, and the data processing and communication device 330 may include circuits (a data processor) for processing data based on sensing information. For example, the data processing and communication device 330 may include the data processor 120 described above with reference to the example embodiments of FIGS. 1, 2, and 3. In addition, the data processing and communication device 330 may further include a communication circuit (a communication device) for communicating a result of processing the sensing information to another component in the electronic device 300 (e.g., a display) or to another external device on an outer portion of the electronic device 300. According to some example embodiments, the data processor and the communication device may be provided as separate components from each other.

The electronic device 300 may include a connection controller, such as the connection controller 130 described above with reference to the example embodiment of FIG. 1, which may include a plurality of conductive lines and terminals electrically connected to the conductive lines. For example, the plurality of conductive lines may be connected to the power supplier 320, the data processing and communication device 330, and the clock generator 340, and the terminals may be formed on an outer surface of the pop-up device 310. Also, the pop-up device 310 may receive the electric power and the clock signal via the terminals, and may provide the electric power and the clock signal to the gas sensor 311. In addition, the sensing information from the gas sensor 311 may be provided to the data processing and communication device 330 via the terminals and the conductive lines.

As shown on the left of FIG. 8A, the conductive lines and the terminals may be electrically insulated from each other (disabled or disconnected) in a state where the pop-up device 310 is inserted into the electronic device 300 (the inserted state). On the other hand, as shown on the right of FIG. 8A, in a state in which the pop-up device 310 is at least partially exposed to the outer portion of the electronic device 300 (the pop-up state), the conductive lines and the terminals may be electrically connected to each other by contact with each other. FIG. 8A shows a non-limiting example, in which the conductive lines physically contact the terminals when the location of the pop-up device 310 moves from the inserted state to the pop-up state according to manipulation of a user, but according to some other example embodiments, the internal components of the electronic device 300 and the pop-up device 310 may be electrically connected to each other in various ways. As another non-limiting example, conductive units (e.g., additional pads or terminals) may be arranged at one of the ends of the conductive lines connected to the terminals of the pop-up device 310 in order to be easily or strongly coupled to the terminals, and the conductive lines may be connected to the terminals of the pop-up device 310 via the additional pads or terminals.

In addition, FIG. 8B shows an example of connecting the conductive lines to the terminals (e.g., first terminals) of the pop-up device 310, and the electronic device 300 may include a hole into which the pop-up device 310 may be inserted. Also, additional terminals (e.g., second terminals) connected to ends of the conductive lines connected to the power supplier 320, the data processing and communication device 330, and the clock generator 340 may be formed in (or on) an internal surface (surface facing the pop-up device 310) inside the hole, and the second terminals may physically connect to the first terminals of the pop-up device 310 when in the pop-up state. The first terminals and the second terminals may be implemented in various types, which may be the same type or different types, and at least one of the first terminals and the second terminals is implemented as a conductive unit having elasticity so that the first terminals and the second terminals may be stably connected to each other.

In addition, FIGS. 8A and 8B illustrate a non-limiting example of an electrode of a contact electric conductive type, but according to some other example embodiments, various contactless electric conductive types (e.g., an electromagnetic type, an optical type, a sound wave type, etc.) may be implemented.

Figure 9:
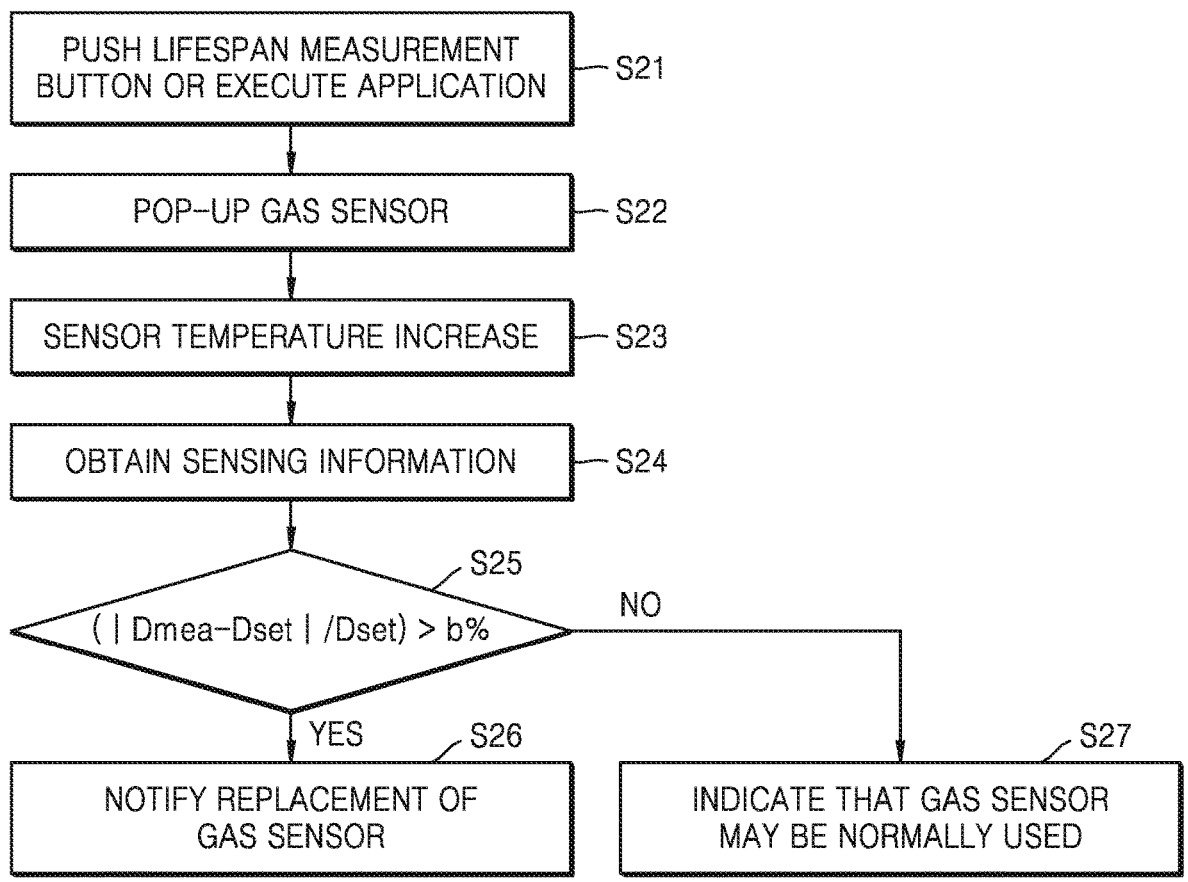
FIG. 9 is a flowchart illustrating an example of determining the lifespan of a gas sensor mounted in an electronic device according to some example embodiments.

FIG. 9 is a flowchart illustrating an example of determining the lifespan of a gas sensor mounted in an electronic device according to some example embodiments.

Referring to FIG. 9, the gas sensor including the FBAR may be replaced, due to contamination, performance degradation, and/or when the end of the lifespan thereof is reached, for example. According to some example embodiments, the gas sensor may be replaced by replacing the pop-up device in which the gas sensor is mounted.

First, a measurement of the lifespan of the gas sensor may be triggered, such as by pushing a lifespan measurement button provided on the electronic device and/or by executing an application installed on the electronic device (S21).

The lifespan of the gas sensor may be measured by various methods. For example, the pop-up device (or the gas sensor mounted in the pop-up device) may be switched to the pop-up state in response to the triggering of the lifespan measurement (S22). Accordingly, the electric power and the clock signal may be supplied to the gas sensor mounted in the pop-up device according to the above-described example embodiments.

As a non-limiting example, when the electric power is supplied to the gas sensor, heat may be applied to the gas sensor, and accordingly, the temperature of the gas sensor may increase (S23). Also, sensing information may be obtained according to the above-described example embodiments in a state where the temperature of the gas sensor is increased (S24). For example, in the state where the temperature of the gas sensor is increased, the sensing information may be obtained based on a frequency counting operation performed on the oscillating signals output from the oscillator block in the gas sensor. Also, in a pop-up state of the pop-up device, the sensing information from the gas sensor may be provided to a calculation device on an outer portion of the pop-up device. For example, sensing information that may be used to determine lifespan may be provided to an application processor in the electronic device, such as the application processor 150 according to the example embodiments described above with reference to FIG. 2.

When releasing the gas sensor, data (e.g., setting data) based on sensing information from a normal gas sensor at a certain temperature (e.g., a baseline or normal temperature) may be stored in a storage device (not shown) in the electronic device, and data (e.g., measurement data) based on the sensing information obtained in the above-described process may be compared with the setting data stored in advance on the electronic device (S25). For example, measurement data Dmea may be compared with setting data Dset to determine the lifespan of the gas sensor, and whether to replace the gas sensor may be determined based on a comparison result. FIG. 9 shows a non-limiting example of a comparing operation, that is, when a difference value between the measurement data Dmea and the setting data Dset is greater than the setting data Dset by a predetermined critical value (or desired threshold percentage) b %, it may be determined that the gas sensor has reached (or is nearing) the end of its lifespan and needs to be (or should be) replaced.

According to the determination result at S25, various operations may be performed by a control of the application processor in the electronic device. For example, when the determination result indicates that the predetermined critical value (or desired threshold percentage) has been exceeded (Yes at S25), a notification indicating that the gas sensor needs to be (or should be) replaced may be provided (S26). For example, replacement of the gas sensor may be notified to the user by controlling a display operation, an LED display, a voice output, etc. On the other hand, when the determination result indicates that the predetermined critical value (or desired threshold percentage) has not been exceeded (No at S25), an indication that the gas sensor may be normally used may be provided (S27). For example, normal use of the gas sensor may be notified to the user by controlling a display operation, an LED display, a voice output, etc.

When determining the lifespan of the gas sensor in the above-described example embodiment, the lifespan determination operation may be performed on each of a plurality of sensors (e.g., FBAR sensors) included in the gas sensor, and it may be determined that the gas sensor has reached the end of its lifespan when one or more of the plurality of FBAR sensors has reached the end of their lifespan, for example.

Figure 10:
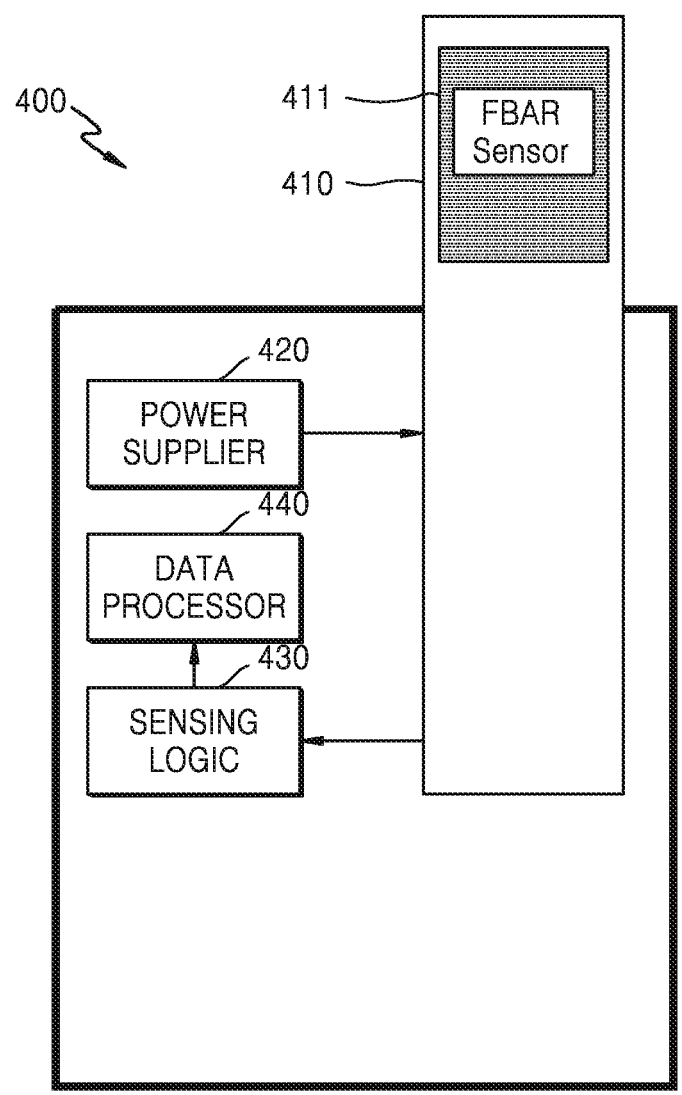
FIG. 10 is a block diagram of an electronic device according to a modified example embodiment.

FIG. 10 is a block diagram of an electronic device 400 according to a modified example embodiment.

Referring to FIG. 10, the electronic device 400 may include a pop-up device 410 in which a gas sensor 411 is mounted, a power supplier 420, a sensing logic 430, and a data processor 440. Various components may enable sensing the gas according to the above-described example embodiments, and some of the components may be formed in the pop-up device 410 and some other components may be provided on an outer portion of the pop-up device 410. As a non-limiting example, the components for enabling the gas sensing operation may include the FBAR sensor and the sensing logic 430 for generating the sensing information according to the sensing of the gas by the FBAR sensor, and in the example embodiment of FIG. 10, the gas sensor 411 may be defined as a concept including only the FBAR sensor. Also, as a component related to the gas sensing operation, the oscillator in the above-described example embodiments may be included, and the oscillator may be formed in the pop-up device 410 and included in the gas sensor 411 according to some example embodiments, or may be defined as a component provided on the outer portion of the pop-up device 410 according to some other example embodiments.

According to some example embodiments, the electric power may be supplied to the gas sensor 411 in the inserted state, or the supply of the electric power may be blocked (disabled or prevented) in the pop-up state, according to the state of the pop-up device 410 in relation to the electronic device 400 (that is, according to the location of the pop-up device 410 with respect to the electronic device 400). Although not shown in FIG. 10, connections between various other devices (e.g., a clock generator) and the gas sensor 411 may be controlled according to the state of the pop-up device 410 (the inserted state or the pop-up state). Also, since the sensing logic 430 may be provided on the outer portion of the pop-up device 410, the sensing logic 430 may receive the electric power and the clock signal regardless of the state of the pop-up device 410 (that is, the electric power and the clock signal may be supplied to the sensing logic 430 in both the inserted state and the pop-up state).

As a non-limiting example, when the pop-up device 410 is in the pop-up state, the electric power is supplied to the gas sensor 411, and communication between the gas sensor 411 and the sensing logic 430 may be activated (or enabled). A gas sensing result (e.g., oscillating signal of the oscillator) may be provided from the gas sensor 411 to the sensing logic 430, and the sensing logic 430 may generate sensing information based on the counting operation on the oscillating signal according to the above-described example embodiments and may provide the sensing information to the data processor 440. In the structure shown in FIG. 10, as a non-limiting example, since the data processor 440 receives the sensing information from the sensing logic 430 provided on the outer portion of the pop-up device 410, the gas sensor 411 and the data processor 440 may not communicate with each other.

Figure 11A:
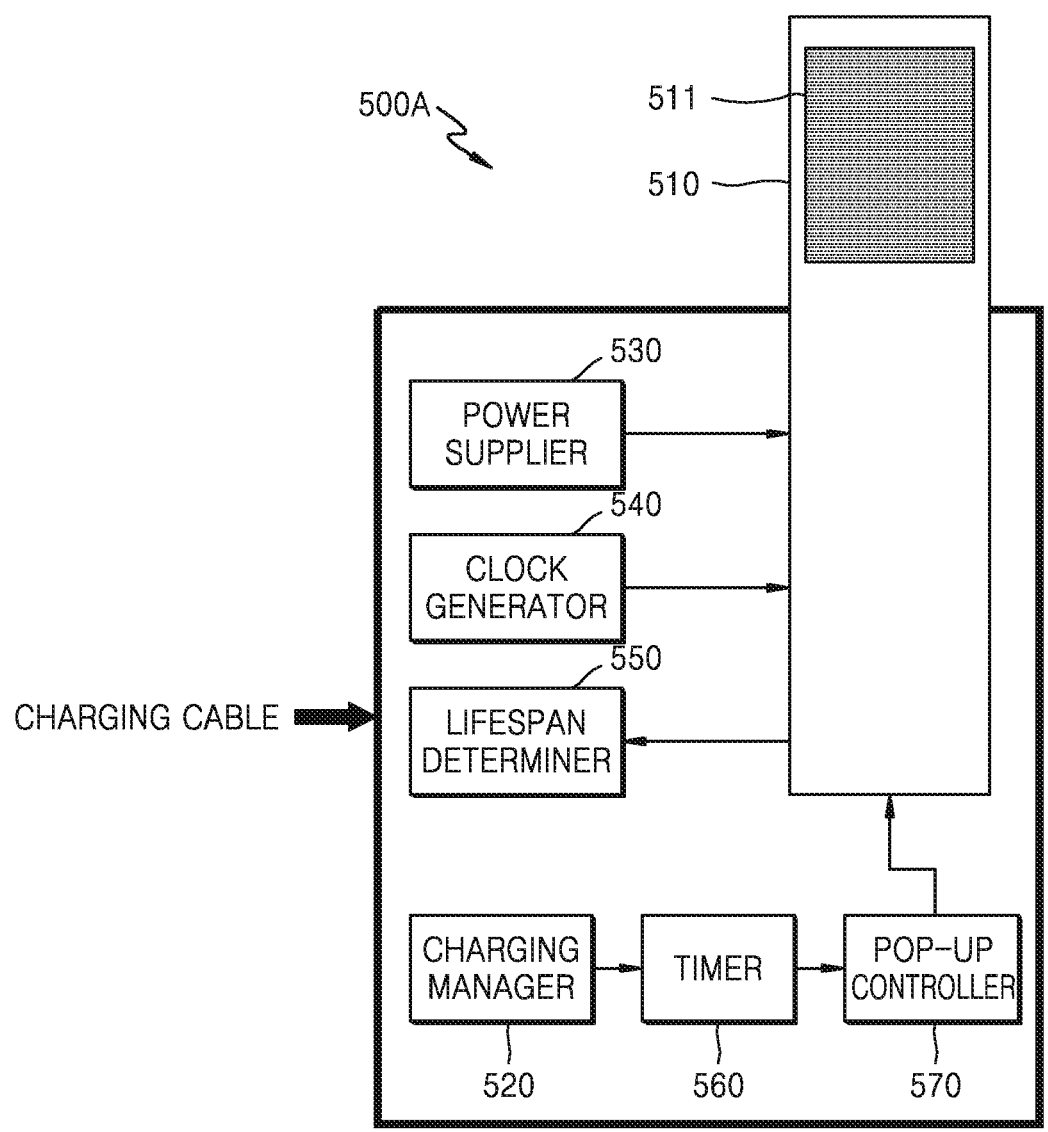
FIGS. 11A and 11B are block diagrams showing various examples of an operation of determining the lifespan of a gas sensor in an electronic device.
Figure 11B:
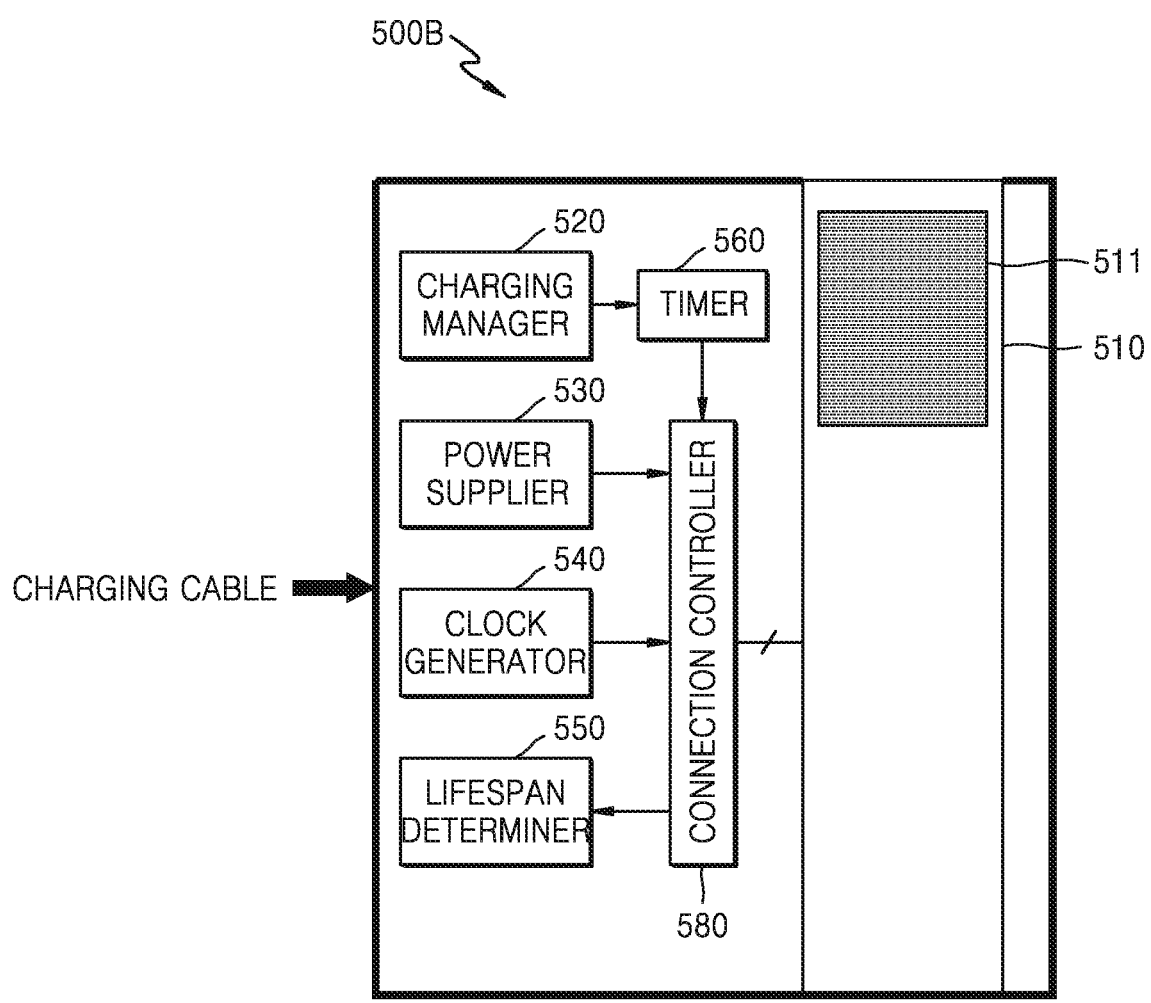

FIGS. 11A and 11B are block diagrams showing various examples of an operation of determining the lifespan of a gas sensor 511 in an electronic device 500A. FIGS. 11A and 11B show an example embodiment in which the electronic device itself automatically determines the lifespan of the gas sensor, regardless of a user's selection (that is, without requiring the user to manually push a lifespan measurement button provided on the electronic device or cause execution of an application installed on the electronic device to trigger the lifespan measurement).

Referring to FIG. 11A, the electronic device 500A may include a pop-up device 510 in which the gas sensor 511 is mounted, a charging manager 520, a power supplier 530, a clock generator 540, a lifespan determiner 550, a timer 560, and a pop-up controller 570. In addition, other components such as the data processor of the above-described example embodiments may be further included in the electronic device 500A.

The electronic device 500A may determine the lifespan of the gas sensor 511 by itself based on a predetermined (or desired) time period or according to a predetermined (or desired) circumstance or condition, regardless of the user's selection. For example, in a pop-up state of the pop-up device 510, when the electric power is supplied to the gas sensor 511 and heat is applied to the FBAR sensor (not shown), whether to replace the gas sensor 511 may be determined by using the calculation using the sensing information as described above.

According to some example embodiments, when a charging cable is connected to the electronic device 500A, the pop-up device 510 may be controlled to switch to the pop-up state at a certain time point (or after a predetermined or desired time period has passed) during the charging of the electronic device 500A. As a non-limiting example, information indicating the charging state is provided from the charging manager 520 to the timer 560, the timer 560 outputs information indicating a time point of the lifespan determination to the pop-up controller 570, and the pop-up controller 570 may switch the pop-up device 510 to the pop-up state through an electrical or physical control, regardless of manipulation of the user (that is, without requiring the user to manually switch the pop-up device 510 to the pop-up state).

In addition, when the pop-up device 510 is switched to the pop-up state by the pop-up controller 570, the electric power and the clock signal may be supplied to the gas sensor 511 in the same or similar way as in the above-described example embodiments, and the lifespan determiner 550 may communicate with the gas sensor 511. The lifespan determiner 550 may perform a lifespan determination operation based on the sensing information from the gas sensor 511.

FIG. 11B shows an example embodiment, in which the lifespan determining operation is performed by the lifespan determiner 550 in a state where the pop-up device is inserted into an electronic device 500B (the inserted state). As a non-limiting example, the lifespan of the gas sensor 511 may be determined without switching the pop-up device 510 to the pop-up state, because the lifespan of the gas sensor 511 may be determined based on the sensing information that is generated by applying heat to the sensor block of the gas sensor 511 without exposing the sensor block to the outside (the outer portion) of the electronic device 500B.

Referring to FIG. 11B, the electronic device 500B may include the pop-up device 510 in which the gas sensor 511 is mounted, the charging manager 520, the power supplier 530, the clock generator 540, the lifespan determiner 550, the timer 560, and a connection controller 580. Detailed descriptions for the components of the electronic device 500B in FIG. 11B, which have been described already above, are omitted.

The lifespan determining operation may be performed at a predetermined (or desired) time point during the charging of the electronic device 500B, and to perform the lifespan determining operation, a connecting state of the connection controller 580 may be adjusted based on information from the charging manager 520 and the timer 560. For example, the conductive lines and terminals may physically contact each other when locations of the conductive lines and/or the terminals change when the pop-up device 510 switches to the pop-up state, according to the above-described example embodiments. The physical contact between the conductive lines and the terminals may be prevented (disconnected) in a state in which the pop-up device 510 is inserted into the electronic device 500B (in the inserted state).

With the connection structure for the physical contact as described above, the connection controller 580 may further include additional components (or additional connection structure), connecting states of which are controlled based on the above-described information for determining lifespan, for example, switches (not shown) for electrically connecting the power supplier 530, the clock generator 540, and the lifespan determiner 550 with the gas sensor 511. When the connection controller 580 has a connection state for determining the lifespan of the gas sensor 511, the electric power and the clock signal may be provided to the gas sensor 511 in a state where the pop-up device 510 is inserted in the electronic device 500B (the inserted state), and communication between the lifespan determiner 550 and the gas sensor 511 may be allowed (or enabled). The lifespan determiner 550 may perform a lifespan determination operation based on the sensing information from the gas sensor 511.

In the example embodiments shown in FIGS. 11A and 11B, the pop-up controller 570 and the connection controller 580 are controlled based on the information from the charging manager 520 and the timer 560 in a state of charging the electronic device 500A or 500B, but some other example embodiments are not limited thereto. For example, in the electronic device 500A or 500B, various other circumstances or conditions (e.g., a condition of satisfying a predetermined or desired time period, a condition in which the electronic device is not being used by the user, etc.) are determined, and then the electronic device 500A or 500B may be configured so that the operation for determining the lifespan of the gas sensor 511 may be electrically controlled regardless of whether the pop-up device 510 is in the pop-up state (that is, the lifespan measurement may be performed even when the pop-up device 510 is in the inserted state).

Figure 12:
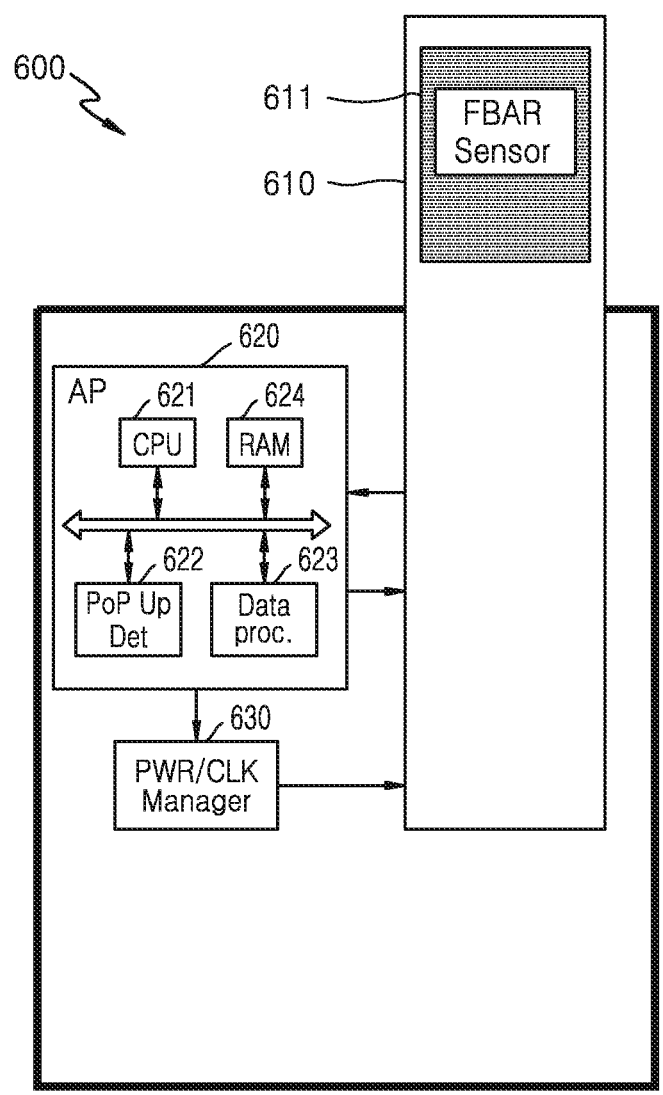
FIG. 12 is a block diagram of an example of an electronic device, in which an operation of a gas sensor is controlled by an application processor, according to some example embodiments.

FIG. 12 is a block diagram of an example of an electronic device 600, in which an operation of a gas sensor 611 is controlled by an application processor 620, according to some example embodiments.

Referring to FIG. 12, the electronic device 600 may include the pop-up device 610, in which the gas sensor 611 is mounted, an application processor 620, and a power/clock manager 630. The gas sensor 611 may include various elements including the FBAR sensor, and according to the above-described example embodiments, may further include an oscillator block and a sensing logic (not shown).

The application processor 620 may be implemented as a system-on-chip, for example, and may control overall operations of the electronic device 600, as well as the gas sensing operation. For example, the application processor 620 may include a central processing unit (CPU) 621, a pop-up determiner 622, a data processor 623, and random access memory (RAM) 624. In addition, the application processor 620 may further include various kinds of functional blocks such as a display controller, read only memory (ROM), a memory controller, a modem, a graphic processing unit (GPU), etc., which are omitted in FIG. 12 for convenience of description.

The CPU 621 may process or execute programs or data stored on the ROM and/or RAM 624. For example, the CPU 621 may process or execute the programs and data according to an operating clock. The CPU 621 may be implemented as a multi-core processor, for example. The multi-core processor is a computing component having two or more independent processors (e.g., cores), and each of the processors (or cores) may read and execute program instructions. In addition, the RAM 624 may temporarily store programs, data, and/or instructions. For example, programs and/or data stored on the ROM may be temporarily stored on the RAM 624 according to a control of the CPU 621. The RAM 624 may be implemented as a memory, such as dynamic RAM (DRAM) or static RAM (SRAM), for example.

According to some example embodiments, the pop-up determiner 622 may determine a state of the pop-up device 610 in relation to the electronic device 600 (that is, the location of the pop-up device 610 with respect to the electronic device 600), and the application processor 620 may control the power/clock manager 630 according to a determination result of the pop-up determiner 622. As a non-limiting example, when the pop-up device 610 is in the pop-up state, the application processor 620 may control the power/clock manager 630 so that the power/clock manager 630 may provide the electric power and the clock signal to the gas sensor 611. Also, the data processor 623 may perform the data processing operation by using the sensing information provided from the gas sensor 611, and the application processor 620 may perform the above-described post-processes according to the sensing information (or data processing result). On the other hand, when the pop-up device 610 is in the inserted state, the application processor 620 may control the power/clock manager 630 so that the power/clock manager 630 does not provide the electric power and the clock signal to the gas sensor 611, the gas sensor 611 does not generate sensing information, the data processor 623 does not perform a data processing operation, and the application processor 620 does not perform post-processes.

According to some example embodiments, the power/clock manager 630 may be implemented as a separate integrated circuit for managing the electric power and the clock signal, and accordingly, may be implemented as a semiconductor chip separate from the application processor 620, for example. Also, the determination of the state of the pop-up device 610 (the pop-up state or the inserted state) and/or the operation of processing the sensing information according to the above-described example embodiments may be performed by a circuit operation (that is, by hardware), or by executing a program (that is, by software). As a non-limiting example, when the determination of the state of the pop-up device 610 (the pop-up state or the inserted state) and the sensing information processing operation are performed by software, the pop-up determiner 622 and the data processor 623 may include programs for executing the above-described functions, and the programs are loaded on the RAM 624 and the CPU 621 executes the programs loaded on the RAM 624 to perform the functions according to the above-described example embodiments.

In addition, in the above-described example embodiments, the gas sensor is shown as the sensor (FBAR sensor) mounted in the pop-up device, but some other example embodiments are not limited thereto. For example, the sensor mounted in the pop-up device may include various other kinds of sensors, such as a humidity sensor, a temperature sensor, etc., and when operating each of the other kinds of sensors, the supplying of the electric power, the clock signal, and various information to each of the other kinds of sensors may be controlled according to the state of the pop-up device in relation to the electronic device (that is, based on whether the pop-up device is in the inserted state or the pop-up state with respect to the electronic device), as described in the above example embodiments.

Also, the gas sensor is mounted in the pop-up device in the above-described example embodiments, but some other example embodiments are not limited thereto. For example, when a device for protruding a part thereof to the outside (e.g., semi-detaching device) is included in the electronic device, the gas sensor may be mounted in the semi-detaching device.

Units and/or devices according to example embodiments may be implemented using hardware, a combination of hardware and software, or storage media storing software. Hardware may be implemented using processing circuitry such as, but not limited to, one or more processors, one or more Central Processing Units (CPUs), one or more controllers, one or more arithmetic logic units (ALUs), one or more digital signal processors (DSPs), one or more microcomputers, one or more field programmable gate arrays (FPGAs), one or more System-on-Chips (SoCs), one or more programmable logic units (PLUs), one or more microprocessors, one or more Application Specific Integrated Circuits (ASICs), or any other device or devices capable of responding to and executing instructions in a defined manner.

Software may include a computer program, program code, instructions, or some combination thereof, for independently or collectively instructing or configuring a hardware device to operate as desired. The computer program and/or program code may include program or computer-readable instructions, software components, software modules, data files, data structures, etc., capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., one or more processors, CPUs, controllers, ALUs, DSPs, microcomputers, microprocessors, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor. In another example, the hardware device may be an integrated circuit customized into special purpose processing circuitry (e.g., an ASIC).

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as one computer processing device; however, one skilled in the art will appreciate that a hardware device may include multiple processing elements and multiple types of processing elements. For example, a hardware device may include multiple processors or a processor and a controller. In addition, other processing configurations are possible, such as parallel processors.

Software and/or data may be embodied permanently or temporarily in any type of storage media including, but not limited to, any machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including tangible or non-transitory computer-readable storage media as discussed herein.

Storage media may also include one or more storage devices at units and/or devices according to one or more example embodiments. The one or more storage devices may be tangible or non-transitory computer-readable storage media, such as random access memory (RAM), read only memory (ROM), a permanent mass storage device (such as a disk drive), and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the storage media, the computer programs, program code, instructions, or some combination thereof, may be specially designed and constructed for the purposes of the example embodiments, or they may be known devices that are altered and/or modified for the purposes of example embodiments.

While the inventive concepts have been particularly shown and described with reference to some example embodiments thereof, it will be understood that various changes in form and details may be made therein without departing from the spirit and scope of the following claims according to some other example embodiments of the inventive concepts.

What is claimed is:

1. An electronic device comprising:
   a pop-up device configured to be inserted into a main body of the electronic device in an inserted state of the pop-up device and comprising a gas sensor including a sensor block for sensing a gas, the pop-up device being configured to expose the sensor block to an outer portion of the electronic device in a pop-up state of the pop-up device in which at least a part of the pop-up device protrudes outward from the electronic device;
   a power supplier arranged on an outer portion of the pop-up device, the power supplier being configured to supply electric power to the gas sensor; and
   a connection controller configured to control a connection state of the connection controller, so as to block supply of the electric power to the gas sensor when the pop-up device is in the inserted state, and to supply the electric power to the gas sensor when the pop-up device is in the pop-up state,
   wherein the connection controller comprises one or more terminals formed on the pop-up device, and the one or more terminals move together with the pop-up device when the pop-up device moves.

2. The electronic device of claim 1, further comprising a data processor configured to receive sensing information indicating a gas sensing result from the gas sensor in the pop-up state of the pop-up device,
   wherein, when the pop-up device is in the inserted state, the connection controller controls the connection state so that communication between the data processor and the gas sensor is blocked, and
   when the pop-up device is in the pop-up state, the connection controller controls the connection state to allow the data processor and the gas sensor to communicate with each other.

3. The electronic device of claim 1, wherein the sensor block comprises one or more film bulk acoustic resonator (FBAR) sensors.

4. The electronic device of claim 3, wherein the gas sensor further comprises:
   an oscillator block comprising one or more oscillators that are arranged corresponding to the one or more FBAR sensors, and are configured to generate oscillating signals having different frequencies from one another according to gas sensing states of the one or more FBAR sensors; and
   a sensing logic configured to output sensing information indicating a gas sensing result based on detection of the frequencies of the oscillating signals.

5. The electronic device of claim 4, wherein, when the pop-up device is in the pop-up state, the sensor block is exposed to the outer portion of the electronic device, and the oscillator and the sensing logic remain inside the main body of the electronic device or are selectively exposed to the outer portion of the electronic device.

6. The electronic device of claim 1, further comprising a clock generator configured to generate a clock signal used in a gas sensing operation of the gas sensor,
   wherein the connection controller controls the connection state to block supply of the clock signal to the gas sensor when the pop-up device is in the inserted state, and to allow the clock signal to be provided to the gas sensor when the pop-up device is in the pop-up state.

7. The electronic device of claim 1, wherein
   the gas sensor further comprises an oscillator block configured to generate oscillating signals having different frequencies from one another according to a gas sensing state of the sensor block; and
   the electronic device further comprises a sensing logic arranged on an outer portion of the pop-up device, the sensing logic being configured to output sensing information indicating a gas sensing result based on detection of the frequencies of the oscillating signals,
   wherein the sensing logic receives electric power supplied from the power supplier regardless of whether the pop-up device is in the inserted state or the pop-up state.

8. The electronic device of claim 1, further comprising a communication device configured to provide data including a gas sensing result of the gas sensor to a device inside or outside the electronic device,
   wherein the connection controller is configured to control the connection state to disconnect the gas sensor from the communication device when the pop-up device is in the inserted state, and to connect the gas sensor to the communication device when the pop-up device is in the pop-up state.

9. The electronic device of claim 1, being a smartphone, wherein the pop-up device comprises a stylus pen that is configured to be inserted into the smartphone.

10. The electronic device of claim 1, wherein the connection controller further comprises a conductive line electrically connected to the power supplier, the conductive line being arranged on a fixed location in the electronic device, and
   when the pop-up device is switched to the pop-up state from the inserted state, the one or more terminals move together with the pop-up device so as to be physically connected to the conductive line.

11. The electronic device of claim 1, wherein the connection controller is configured to connect the power supplier to the gas sensor in a contactless electric conductive type when the pop-up device is in the pop-up state.

12. The electronic device of claim 1, further comprising a lifespan determiner configured to determine a lifespan of the gas sensor based on sensing information provided from the gas sensor, in a state where heat is applied to the sensor block when the electric power is supplied to the gas sensor.

13. The electronic device of claim 12, wherein an operation of determining the lifespan of the gas sensor is performed during charging of the electronic device, when the pop-up device is switched to the pop-up state from the inserted state, or when the electric power is supplied to the gas sensor via an additional connection structure in the connection controller when the pop-up device is in the inserted state.

14. An electronic device comprising:
a pop-up device configured to be inserted into a main body of the electronic device in an inserted state of the pop-up device and comprising a gas sensor for sensing a gas, the pop-up device being configured to expose the gas sensor at least partially to an outer portion of the electronic device in a pop-up state of the pop-up device in which at least a part of the pop-up device protrudes outward from the electronic device and comprising a plurality of first terminals formed on an outer surface of the pop-up device to be electrically connected to an external device;
a power supplier configured to supply electric power to the gas sensor;
a clock generator configured to generate a clock signal that is used in a gas sensing operation of the gas sensor;
a first conductive line electrically connected to the power supplier; and
a second conductive line electrically connected to the clock generator,
wherein connections between the first conductive line and the second conductive line, and the plurality of first terminals of the pop-up device, are disconnected when the pop-up device is in the inserted state, and
the first conductive line and the second conductive line are physically connected to the plurality of first terminals when the pop-up device is in the pop-up state.

15. The electronic device of claim 14, wherein
a plurality of second terminals are further arranged on an outer surface of a hole that is formed in the main body of the electronic device to allow the pop-up device to be inserted into the main body, and
when the pop-up device is in the pop-up state, the second terminals are configured to contact the plurality of first terminals, such that the first conductive line and the second conductive line are connected to the plurality of first terminals via the plurality of second terminals to supply the electric power and the clock signal to the gas sensor.

16. The electronic device of claim 14, wherein the gas sensor comprises:
a sensor block comprising one or more film bulk acoustic resonator (FBAR) sensors; and
a sensing logic configured to generate and output sensing information according to a gas sensing state of the sensor block.

17. The electronic device of claim 16, wherein, when the pop-up device is in the pop-up state, the sensor block is exposed to the outer portion of the electronic device, and the sensing logic is located inside the main body of the electronic device.

18. A method of operating an electronic device, the electronic device comprising a pop-up device configured to be inserted into a main body of the electronic device in an inserted state of the pop-up device, the pop-up device comprising a gas sensor configured to be exposed at least partially to an outer portion of the electronic device in a pop-up state of the pop-up device in which at least a part of the pop-up device protrudes outward from the electronic device, the method comprising:
determining whether the pop-up device is in the pop-up state or the inserted state;
in response to determining that the pop-up device is in the pop-up state,
supplying electric power and a clock signal to the gas sensor mounted in the pop-up device from a circuit arranged on the outer portion of the pop-up device, and
outputting sensing information indicating a gas sensing result to the circuit on the outer portion of the pop-up device; and
in response to determining that the pop-up device is in the inserted state, blocking supply of the electric power and the clock signal to the gas sensor mounted in the pop-up device.

19. The method of claim 18, further comprising controlling a display operation for indicating the gas sensing result, performed by the circuit on the outer portion of the pop-up device, based on a data processing result generated by using the sensing information.

20. The method of claim 18, further comprising:
entering a charging state of the electronic device when a charging cable is connected to the electronic device;
supplying the electric power and the clock signal to the gas sensor at a certain time point during the charging state; and
determining a lifespan of the gas sensor through a calculation using the sensing information from the gas sensor and data stored on the electronic device.

* * * * *